United States Patent [19]
Aristoff

[11] Patent Number: 4,668,814
[45] Date of Patent: May 26, 1987

[54] INTERPHENYLENE CARBACYCLIN DERIVATIVES

[75] Inventor: Paul A. Aristoff, Portage, Mich.

[73] Assignee: The Upjohn Company, Kalamazoo, Mich.

[21] Appl. No.: 690,803

[22] Filed: Jan. 11, 1985

[51] Int. Cl.[4] .......................................... C07C 177/00
[52] U.S. Cl. .................................. 560/51; 544/155;
544/380; 546/203; 546/204; 546/283; 546/284;
546/285; 548/540; 549/66; 549/78; 549/79;
549/305; 549/465; 549/496; 549/499; 549/501;
549/502; 549/65; 560/45; 560/56; 562/444;
562/466; 562/499; 562/453; 564/80; 564/88;
564/89; 564/90; 564/92; 564/93; 564/95;
564/97; 564/98; 564/99; 564/152; 564/158;
564/171; 564/174; 564/374; 564/384; 564/427;
564/453; 564/454; 568/633; 568/808; 568/817
[58] Field of Search ............................ 560/51, 45, 56;
562/444, 466, 499, 453; 542/429; 544/155, 380;
564/80, 88, 89, 90, 92, 93, 95, 97, 98, 99, 171,
174, 152, 158, 374, 384, 427, 453

[56] References Cited

U.S. PATENT DOCUMENTS

| | | | |
|---|---|---|---|
| 4,180,657 | 12/1979 | Sih | 542/426 |
| 4,192,891 | 3/1980 | Haslanger | 424/305 |
| 4,225,508 | 9/1980 | Sih | 260/346.22 |
| 4,238,414 | 12/1980 | Morton | 564/453 |
| 4,306,075 | 12/1981 | Aristoff | 560/56 |
| 4,306,076 | 12/1981 | Nelson | 560/56 |
| 4,349,689 | 9/1982 | Aristoff | 560/117 |

FOREIGN PATENT DOCUMENTS

| | | |
|---|---|---|
| 0024943 | 11/1981 | European Pat. Off. . |
| 0087237 | 8/1983 | European Pat. Off. . |
| 2900352 | 7/1979 | Fed. Rep. of Germany . |
| 4063059 | 5/1979 | Japan . |
| 4063060 | 5/1979 | Japan . |
| 4024865 | 5/1979 | Japan . |
| 2012265 | 7/1979 | United Kingdom . |
| 2013661 | 8/1979 | United Kingdom . |
| 2017699 | 10/1979 | United Kingdom . |
| 2070596 | 9/1981 | United Kingdom . |

OTHER PUBLICATIONS

Aristoff, P. A., et al., Advances in Prostaglandin, Thromboxane, and Leukotriene Research, 11, 1983, pp. 267–274, "Synthesis and Structure–Activity Relationship of Novel Stable Prostacyclin Analogs".

Aristoff, P. A. and Harrison, A. W., Tetrahedron Letters, 23 (No. 20), 1982; pp. 2067–2070, "Synthesis of Benzindene Prostaglandins: A Novel Potent Class of Stable Prostacyclin Analogs".

Aristoff, P. A., J. Org. Chem., 46 (No. 9), 1981, pp. 1954–1957, "Practical Synthesis of 6a–Carbaprostaglandin $I_2$".

Barco, A., et al., J. Org. Chem., 45 (No. 32), 1980, pp. 4776–4778, "A New Elegant Route to a Key Intermediate for the Synthesis of 9(O)-Methanoprostacyclin".

Konishi, Y., et al., Chem. Lett., 1979, pp. 1437–1440, "A Synthesis of 9(O)-Methanoprostacyclin".

Kojima, K. and Sakai, K., Tetrahedron Letters, 39, 1978, pp. 3743–3746, "Total Synthesis of 9(O)-Methanoprostacyclin and Its Isomers".

Morton, D. R., Jr. and Brokaw, F. C., J. Org. Chem., 44 (No. 16), 1979, pp. 2880–2887, "Total Synthesis of 6a–Carbaprostaglandin $I_2$ and Related Isomers".

Nicolaou, K. C., et al., J.C.S. Chem. Comm., 1978, pp. 1067–1068, "Total Synthesis of Carboprostacyclin, A Stable and Biologically Active Analogue of Prostacyclin ($PGI_2$)".

Shibasaki, M., et al., Chem. Lett., 1979, pp. 1299–1300, "A Stereo and Regiospecific Route to the Synthetic Intermediate for the Synthesis of 9(O)-Methanoprostacyclin".

Shibasaki, M., et al., Tetrahedron Letters, 5, 1979, pp. 433–436, "New Synthetic Routes to 9(O)-Methanoprostacyclin, A Highly Stable and Biologically Potent Analog of Prostacyclin".

Skuballa, V. W. and Vorgruggen, H., Agnew. Chem., 93, (No. 12), 1981, pp. 1080–1081, "Ein Neuer Weg Zu 6a–Carbacyclinen–Synthese Eines Stabilen, Biologischpotenten Prostacyclin-Analogons".

Sugie, A., et al., Tetrahedron Letters, 28, 1979, pp. 2607–2610, "Stereocontrolled Approaches to 9(O)-Methanoprostacyclin".

Yamazaki, M., et al., Chem. Lett., 1981, pp. 1245–1248, "1,2-Carbonyl Transposition of cis-Bicyclo[3.3.0]octan-2-one to its 3-One Skeleton: Appl. to Syntheses of $d_1$-Hirsutic Acid and $d_1$-9(O)-Methanoprostacyclin".

Primary Examiner—Paul J. Killos
Attorney, Agent, or Firm—L. Ruth Hattan

[57] ABSTRACT

A compound of the formula

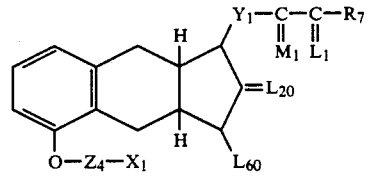

and intermediates useful in preparing same.

11 Claims, No Drawings

INTERPHENYLENE CARBACYCLIN DERIVATIVES

FIELD OF THE INVENTION

The present invention relates to novel pharmaceutically useful compounds which are carbacyclin analogs having a tricyclic nucleus.

PRIOR ART

Related interphenylene carbacyclins are described and claimed in U.S. Pat. No. 4,306,075, U.S. Pat. No 4,306,076, and EP No. 87237 (Derwent No. 754477). Compounds having a 5-membered oxa ring are described in European Pat. No. 24-943 (Derwent No. 19801D).

Carbacyclin and closely related compounds are known in the art. See Japanese Kokai Nos. 63,059 and 63,060, also abstracted respectively as Derwent Farmdoc CPI Numbers 48154B/26 and 48155B/26. See also British published specifications No. 2,012,265 and German Offenlungsschrift No. 2,900,352, abstracted as Derwent Farmdoc CPI Number 54825B/30. See also British published applications Nos. 2,017,699 and 2,013,661 and U.S. Pat. No. 4,238,414.

The synthesis of carbacyclin and related compounds is also reported in the chemical literature, as follows: Morton, D. R., et al, J. Org. Chem., 44:2880-2887 (1979); Shibasaki, M., et al, Tetrahedron Lett., 433-436 (1979); Kojima, K., et al, Tetrahedron Lett., 3743-3746 (1978); Nicolaou, K. C., et al, J. Chem. Soc., Chemical Communications, 1067-1068 (1978); Sugie, A., et al, Tetrahedron Lett., 2607-2610 (1979); Shibasaki, M., Chem. Lett., 1299-1300 (1979), and Hayashi, M., Chem. Lett., 1437-40 (1979); Aristoff, P. A., J. Org. Chem. 46, 1954-1957 (1981); Yamazaki, M., et al, Chem. Lett., 1245-1248 (1981); and Barco, A., et al, J. Org. Chem. 45, 4776-4778 (1980); and Skuballa, W., et al, Angew. Chem. 93, 1080-1081 (1981). The utility and synthesis of compounds closely related to those claimed herein is described in Aristoff, P. A., and Harrison, A. W., Tetrahedron Lett. 23, 2067-2070 (1982) and in Advances in Prostaglandin, Thromboxane, and Leukotriene Research, Vol. 11, 267 (1983).

7-Oxo and 7-hydroxy-CBA$_2$ compounds are apparently disclosed in U.S. Pat. No. 4,192,891. 19-Hydroxy-CBA$_2$ compounds are disclosed in U.S. Pat. No. 4,225,508. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai No. 77/24,865, published Feb. 24, 1979.

SUMMARY OF THE INVENTION

The present invention provides compounds of Formula I wherein:
$X_1$ is
(1) —COOR$_1$, wherein R$_1$ is
  (a) hydrogen;
  (b) (C$_1$-C$_{12}$) alkyl;
  (c) (C$_3$-C$_{10}$) cycloalkyl;
  (d) (C$_7$-C$_{12}$) aralkyl;
  (e) phenyl, optionally substituted with one, 2 or 3 chloro or (C$_1$-C$_3$) alkyl;
  (f) phenyl substituted in the para position by
    (i) —NHCOR$_{25}$,
    (ii) —COR$_{26}$,
    (iii) 
    or
    (iv) —CH=N—NHCONH$_2$ wherein R$_{25}$ is methyl, phenyl, acetamidophenyl, benzamidophenyl, or —NH$_2$; R$_{26}$ is methyl, phenyl, —NH$_2$, or methoxy; R$_{54}$ is phenyl or acetamidophenyl; inclusive; or
  (g) a pharmocologically acceptable cation;
(2) —CH$_2$OH;
(3) —COL$_4$, wherein L$_4$ is
  (a) amino of the formula —NR$_{51}$R$_{52}$ wherein R$_{51}$ and R$_{52}$ are
    (i) hydrogen,
    (ii) (C$_1$-C$_{12}$) alkyl,
    (iii) (C$_3$-C$_{10}$) cycloalkyl,
    (iv) (C$_7$-C$_{12}$) aralkyl,
    (v) phenyl, optionally substituted with one 2 or 3 chloro, (C$_1$-C$_3$) alkyl, hydroxy, carboxy, (C$_2$-C$_5$) alkoxycarbonyl, or nitro,
    (vi) (C$_2$-C$_5$) cyanoalkyl,
    (vii) (C$_2$-C$_5$) carboxyalkyl,
    (viii) (C$_2$-C$_5$) carbamoylalkyl,
    (ix) (C$_3$-C$_6$) acetylalkyl,
    (x) (C$_7$-C$_{11}$) benzoalkyl, optionally substituted by one, 2 or 3 chloro, (C$_1$-C$_3$) alkyl, hydroxy, (C$_1$-C$_3$) alkoxy, carboxy, (C$_2$-C$_5$) alkoxy carbonyl, or nitro,
    (xi) pyridyl, optionally substituted by one, 2 or 3 chloro, (C$_1$-C$_3$) alkyl, or (C$_1$-C$_3$) alkoxy,
    (xii) (C$_6$-C$_9$) pyridylalkyl optionally substituted by one, 2 or 3 chloro, (C$_1$-C$_3$) alkyl, hydroxy, or (C$_1$-C$_3$) alkoxy,
    (xiii) (C$_1$-C$_4$) hydroxyalkyl,
    (xiv) (C$_1$-C$_4$) dihydroxyalkyl,
    (xv) (C$_1$-C$_4$) trihydroxyalkyl, with the proviso that not more than one of R$_{51}$ and R$_{52}$ is other than hydrogen or alkyl;
  (b) cycloamino selected from the group consisting of pyrrolidino, piperidino, morpholino, piperazino, hexamethylenimino, pyrrolino, or 3,4-didehydropiperidinyl optionally substituted by one or 2 (C$_1$-C$_{12}$) alkyl of one to 12 carbon atoms, inclusive;
  (c) carbonylamino of the formula —NR$_{53}$COR$_{51}$ wherein R$_{53}$ is hydrogen or (C$_1$-C$_4$) alkyl and R$_{51}$ is other than hydrogen, but otherwise defined as above;
  (d) sulfonylamino of the formula —NR$_{53}$SO$_2$R$_{51}$, wherein R$_{51}$ and R$_{53}$ are defined in (c);
(4) —CH$_2$NL$_2$L$_3$ wherein L$_2$ and L$_3$ are hydrogen or (C$_1$-C$_4$) alkyl, being the same or different, or the pharmacologically acceptable acid addition salts thereof when X$_1$ is —CH$_2$NL$_2$L$_3$;
(5) —CN;
wherein Z$_4$ is —CH$_2$—, —CH$_2$CH$_2$—, —CF$_2$— or —CH$_2$CF$_2$;
wherein L$_{20}$ is α—OH,β—H; α—H,β—OH; H,H; α—CH$_3$,β—H; α—CH$_2$OH,β—H; =O; or =CH$_2$;
wherein L$_{60}$ is hydrogen or L$_{20}$ and L$_{60}$ taken together form a double bond between positions 10 and 11;
wherein Y$_1$ is —CH$_2$CH$_2$—, —SCH$_2$—, —C≡C—, trans—CH=CH—, or cis—CH=CH—;
wherein taken together is

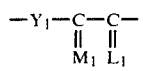

taken together is

wherein $M_1$ is $\alpha$—H:$\beta$—H; =O; $\alpha$—OH:$\beta$—$R_5$; or $\alpha$—$R_5$:$\beta$—OH; wherein $R_5$ is hydrogen or methyl;
wherein $L_1$ is
(1) $\alpha$—$R_3$:$\beta$—$R_4$, $\alpha$—$R_4$:$\beta$—$R_3$, or mixtures thereof wherein $R_3$ and $R_4$ are hydrogen, methyl, or fluoro, being the same or different, with the proviso that one of $R_3$ and $R_4$ is fluoro only when the other is hydrogen or fluoro;
(2) or when $M_1$ is $\alpha$—H:$\beta$—H, $L_1$ is $\alpha$—OH:$\beta$—$R_3$, $\alpha$—$R_3$:$\beta$—OH; or a mixture of $\alpha$—OH:$\beta$—$R_3$ and $\alpha$—$R_3$:$\beta$—OH wherein $R_3$ is hydrogen, methyl, vinyl, or ethynyl;

wherein $R_7$ is
(1) —$C_mH_{2m}CH_3$, wherein m is an integer from one to 8, inclusive;
(2) phenoxy optionally substituted by one, 2 or 3 chloro, fluoro, trifluoromethyl, ($C_1$-$C_3$) alkyl, or ($C_1$-$C_3$) alkoxy, with the proviso that not more than two substituents are other than alkyl with the proviso that $R_7$ is phenoxy or substituted phenoxy, only when $R_3$ and $R_4$ are hydrogen or methyl, being the same or different;
(3) phenyl, benzyl, phenylethyl, or phenylpropyl optionally substituted on the aromatic ring by one, 2 or 3 chloro, fluoro, trifluoromethyl, ($C_1$-$C_3$) alkyl, or ($C_1$-$C_3$) alkoxy, with the proviso that not more than two substituents are other than alkyl;
(4) cis—CH=CH—$CH_2CH_3$;
(5) —$(CH_2)_2$—CH(OH)—$CH_3$;
(6) —$(CH_2)_3$—CH=C$(CH_3)_2$;
(7) —$C_pH_{2p}$CH=$CH_2$ wherein p is an integer from 2 to 6, inclusive;

wherein

taken together is
(1) ($C_4$-$C_7$) cycloalkyl optionally substituted by one to 3 ($C_1$-$C_5$) alkyl, or ($C_1$-$C_5$)alkenyl;
(2) 2-(2-furyl) ethyl;
(3) 2-(3-thienyl) ethoxy;
(4) 3-thienyloxymethyl; or
(5)

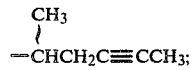

and the individual optical enantiomers thereof with the proviso that each compound is other than one formed when the substituents $X_1$, $Z_4$, $L_{20}$, $Y_1$, $M_1$, $L_1$, and $R_7$ have the following meanings:
$X_1$ is as defined above;
$Z_4$ is —$CH_2$—, —$CF_2$—, or —$CH_2CF_2$—;

$L_{20}$ is $\alpha$—OH,$\beta$—H; $\alpha$—H,$\beta$—OH; H,H; $\alpha$—$CH_2OH$,$\beta$—H;
$Y_1$ is —$CH_2CH_2$—, —C≡C—, trans—CH=CH—, or cis—CH=CH—;
$M_1$ is $\alpha$—OH:$\beta$—$R_5$, or $\alpha$—$R_5$:$\beta$—OH wherein $R_5$ is hydrogen or methyl;
$L_1$ is $\alpha$—$R_3$:$\beta$—$R_4$, $\alpha$—$R_4$:$\beta$—$R_3$, or a mixture thereof wherein $R_3$ and $R_4$ are hydrogen, methyl, or fluoro, being the same or different, with the proviso that one of $R_3$ and $R_4$ is fluoro only when the other is hydrogen or fluoro; and
$R_7$ is as defined above except $R_7$ is other than —$(CH_2)_2$—CH=$CH_2$ and $R_7$ is other than —$C(L_1)R_7$ taken together is as defined above except —$C(L_1)R_7$ is other than ($C_4$-$C_7$)cycloalkyl optionally substituted with ($C_1$-$C_5$)alkenyl.

The present invention also provides a new procedure for preparing compounds of Formula I(a) wherein $X_1$ is
(1) —$COOR_1$, wherein $R_1$ is
  (a) hydrogen;
  (b) ($C_1$-$C_{12}$) alkyl;
  (c) ($C_3$-$C_{10}$) cycloalkyl;
  (d) ($C_7$-$C_{12}$) aralkyl;
  (e) phenyl, optionally substituted with one, 2 or 3 chloro or ($C_1$-$C_3$) alkyl;
  (f) phenyl substituted in the para position by
    (i) —$NHCOR_{25}$,
    (ii) —$COR_{26}$,
    (iii)

or
    (iv) —CH=N—$NHCONH_2$ wherein $R_{25}$ is methyl, phenyl, acetamidophenyl, benzamidophenyl, or —$NH_2$; $R_{26}$ is methyl, phenyl, —$NH_2$, or methoxy; $R_{54}$ is phenyl or acetamidophenyl; inclusive; or
  (g) a pharmacologically acceptable cation;
(2) —$CH_2OH$;
(3) —$COL_4$, wherein $L_4$ is
  (a) amino of the formula —$NR_{51}R_{52}$ wherein $R_{51}$ and $R_{52}$
    (i) hydrogen,
    (ii) ($C_1$-$C_{12}$) alkyl,
    (iii) ($C_3$-$C_{10}$) cycloalkyl,
    (iv) ($C_7$-$C_{12}$) aralkyl,
    (v) phenyl, optionally substituted with one 2 or 3 chloro, ($C_1$-$C_3$) alkyl, hydroxy, carboxy, ($C_2$-$C_5$) alkoxycarbonyl, or nitro,
    (vi) ($C_2$-$C_5$) cyanoalkyl,
    (vii) ($C_2$-$C_5$) carboxyalkyl,
    (viii) ($C_2$-$C_5$) carbamoylalkyl,
    (ix) ($C_3$-$C_6$) acetylalkyl,
    (x) ($C_7$-$C_{11}$) benzoalkyl, optionally substituted by one, 2 or 3 chloro, ($C_1$-$C_3$) alkyl, hydroxy, ($C_1$-$C_3$) alkoxy, carboxy, ($C_2$-$C_5$) alkoxy carbonyl, or nitro,
    (xi) pyridyl, optionally substituted by one, 2 or 3 chloro, ($C_1$-$C_3$) alkyl, or ($C_1$-$C_3$) alkoxy,
    (xii) ($C_6$-$C_9$) pyridylalkyl optionally substituted by one, 2 or 3 chloro, ($C_1$-$C_3$) alkyl, hydroxy, or ($C_1$-$C_3$) alkoxy,
    (xiii) ($C_1$-$C_4$) hydroxyalkyl,
    (xiv) ($C_1$-$C_4$) dihydroxyalkyl, (xv) ($C_1$-$C_4$) trihydroxyalkyl,
with the proviso that not more than one of $R_{51}$ and $R_{52}$ is other than hydrogen or alkyl;
(b) cycloamino selected from the group consisting of pyrrolidino, piperidino, morpholino, piperazino, hexamethylenimino, pyrrolino, or 3,4-didehydropiperidinyl optionally substituted by one or 2 ($C_1$-$C_{12}$) alkyl of one to 12 carbon atoms, inclusive;
(c) carbonylamino of the formula —$NR_{53}COR_{51}$ wherein $R_{53}$ is hydrogen or ($C_1$-$C_4$) alkyl and $R_{51}$ is other than hydrogen, but otherwise defined as above;
(d) sulfonylamino of the formula —$NR_{53}SO_2R_{51}$, wherein $R_{51}$ and $R_{53}$ are defined in (c);
(4) —$CH_2NL_2L_3$ wherein $L_2$ and $L_3$ are hydrogen or ($C_1$-$C_4$) alkyl, being the same or different, or the pharmacologically acceptable acid addition salts thereof when $X_1$ is —$CH_2NL_2L_3$;
(5) —CN;
wherein $Z_4$ is —$CH_2$—, —$CH_2CH_2$—, —$CF_2$— or —$CH_2CF_2$;
wherein $L_{20}$ is α—OH,β—H; α—H,β—OH; H,H; α—$CH_3$,β—H; α—$CH_2OH$,β—H; =O; or =$CH_2$;
wherein $L_{60}$ is hydrogen or $L_{20}$ and $L_{60}$ taken together form a double bond between positions 10 and 11;
wherein $Y_1$ is —$CH_2CH_2$—, —$SCH_2$—, —C≡C—, trans—CH=CH—, or cis—CH=CH—;
wherein

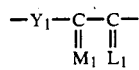

taken together is

wherein $M_1$ is α—H:β—H; =O; α—OH:β—$R_5$; or α—$R_5$:β—OH; wherein $R_5$ is hydrogen or methyl;
wherein $L_1$ is
(1) α—$R_3$:β—$R_4$, α—$R_4$:β—$R_3$, or mixtures thereof wherein $R_3$ and $R_4$ are hydrogen, methyl, or fluoro, being the same or different, with the proviso that one of $R_3$ and $R_4$ is fluoro only when the other is hydrogen or fluoro;
(2) or when $M_1$ is α—H:β—H, $L_1$ is α—OH:β—$R_3$, α'$R_3$:β—OH; or a mixture of α—OH:β—$R_3$ and α—$R_3$:β—OH wherein $R_3$ is hydrogen, methyl, vinyl, or ethynyl;
wherein $R_7$ is
(1) —$C_mH_{2m}CH_3$, wherein m is an integer from one to 8, inclusive;
(2) phenoxy optionally substituted by one, 2 or 3 chloro, fluoro, trifluoromethyl, ($C_1$-$C_3$) alkyl, or ($C_1$-$C_3$)alkoxy, with the proviso that not more than two substituents are other than alkyl with the proviso that $R_7$ is phenoxy or substituted phenoxy, only when $R_3$ and $R_4$ are hydrogen or methyl, being the same or different;
(3) phenyl, benzyl, phenylethyl, or phenylpropyl optionally substituted on the aromatic ring by one, 2 or 3 chloro, fluoro, trifluoromethyl, ($C_1$-$C_3$) alkyl, or ($C_1$-$C_3$) alkoxy, with the proviso that not more than two substituents are other than alkyl;

(4) cis—CH=CH—$CH_2CH_3$;
(5) —($CH_2$)$_2$—CH(OH)—$CH_3$;
(6) —($CH_2$)$_3$—CH=C($CH_3$)$_2$;
(7) $C_pH_{2p}CH=CH_2$ where p is an integer from 2 to 6, inclusive;
wherein

taken together is
(1) ($C_4$-$C_7$) cycloalkyl optionally substituted by one to 3 ($C_1$-$C_5$) alkyl, or ($C_1$-$C_5$)alkyl;
(2) 2-(2-furyl) ethyl;
(3) 2-(3-thienyl) ethoxy;
(4) 3-thienyloxymethyl; or
(5)

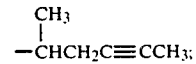

and the individual optical enantiomers thereof.

In the event it is not readily apparent the difference between the compounds of Formula I and those of Formula I(a) lies in the fact that certain compounds of Formula I are excluded by the proviso beginning on page 4, line 35. The compounds excluded by the proviso in Formula I are described and claimed in U.S. Pat. No. 4,306,075 and copending U.S. application Ser. No. 351,069 filed Feb. 22, 1982. The novel process described herein is applicable to the prior claimed compounds and the novel compounds described and claimed herein Also, the present invention provides novel intermediates of Formulas I(b), I(c), I(d) and II as set forth in the Formula Chart. In Formulas I(b) and I(c) the group Q is cis-$CH_2CH=CH_2$, —$CH_2COOH$, or

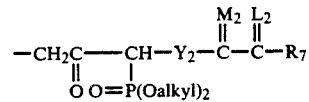

wherein alkyl has from 1 to 4 carbon atoms; L is the same as $L_1$ in Formula I only any hydrous group is protected with an Rx group as defined below; $Y_2$ is —$SCH_2$— or —$CH_2CH_2$—, $M_2$ is α-H,β-ORx, α-ORx,β-H or H,H wherein Rx is a protecting group as defined below, and $R_7$ has the meaning defined in Formula I(a). In Formula I(d) $Q_2$ is

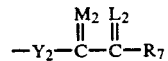

as defined above or $CO_2$ alkyl wherein alkyl has from 1 to 4 carbon atoms. The intermediates of Formulas I(a), I(b), I(c), I(d) and II are useful in the preparation of the compounds of Formuls I and I(a).

The compounds of Formula I and I(a) have useful pharmacological properties as defined below.

DETAILED DESCRIPTION OF INVENTION

In the compounds of the present invention, and as used herein, ('''') denotes the α-configuration, ( ) denotes the β-configuration, (∼) denotes α- and/or β-configuration or the E and/or Z isomer.

With regard to the divalent groups described above, i.e., $L_{20}$, $M_1$ and $L_1$ said divalent groups are defined in terms of an α-substituent and a β-substituent which means that the α-substituent of the divalent group is in the alpha configuration with respect to the plane of the C-8 to $C_{12}$ cyclopentane ring and the β-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety $L_4$ in the —$COL_4$ substituent group the definition $(C_1-C_{12})$alkyl means that $L_4$ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when $L_4$ represents, for example, $(C_2-C_5)$carboxyalkyl, the alkyl moiety thereof contains from 1 to 4 carbon atoms and is a straight chain or a branched chain alkyl group. Similarly a $C_3-C_5$ alkenyl group as may be present on the cycloalkyl group represented by —$C(L_1)R_7$ contains from 3 to 5 carbon atoms and one double bond in the chain.

In Formula I when the hydrogen at position 9 is beta the compounds are named as 9-deoxy-2',9α-methano-3-oxa-4,5,6-trinor-3,7-(1',3'-interphenylene)$PGF_1$ compounds, and when it is alpha the compounds are named as 9-deoxy-2',9β-methano-3-oxa-4,5,6-trinor-3,7-(1',3'-interphenylene)$PGF_1$ compounds.

When $Z_4$ is —$CF_2$— the compounds of Formula I are also characterized as 2,2-difluoro and when $Z_4$ is —$CH_2CF_2$— the compounds are characterized as 2α-homo-2,2-difluoro.

When $R_5$ is methyl, the carbacyclin analogs are all named as "15-methyl-" compounds. Further, except for compounds wherein $Y_1$ is cis-CH=CH—, *compounds wherein the $M_1$* moiety contains an hydroxyl in the beta configuration are additionally named as "15-epi-" compounds.

For the compounds wherein $Y_1$ is cis-CH=CH—, then compounds wherein the $M_1$ moiety contains an hydroxyl in the alpha configuration are named as "15-epi-CBA" compounds. For a description of this convention of nomenclature for identifying C-15 epimers, see U.S. Pat. No. 4,016,184, issued Apr. 5, 1977, particularly columns 24–27 thereof.

The compounds of the present invention which contain —$(CH_2)_2$—, cis-CH=CH—, trans —CH=CH— or —C≡C— as the $Y_1$ moiety, are accordingly referred to as "13,14-dihydro", "cis-13", "trans-13", or —13,14-didehydro" compounds, respectively. Compounds wherein $Y_1$ is —$SCH_2$— are named as "13-thio" compounds.

Compounds wherein $M_1$ is H,H are named as "15-deoxy" compounds. Compounds wherein $M_1$ is =O are named as "15-oxo" compounds.

Compounds wherein $$-Y_1-\underset{M_1}{\overset{||}{C}}-\underset{L_1}{\overset{||}{C}}-$$

taken together is $$-CH=NNHCNH-\overset{O}{\overset{||}{}}$$

are are named as 13,14,15,16,17,18,19,20-octanor-12-[N-$R_7$-carbamoyl)hydrazono-methyl].

When $R_7$ is $$-\underset{H}{\overset{CH_3}{\underset{|}{C}}}-CH_2CH_2CH_2CH_3$$

the compounds so described are named as 17(S),20-dimethyl compounds.

When —$C(L_1)$—$R_7$ is $$-\underset{}{\overset{CH_3}{\underset{|}{CH}}}-CH_2C\equiv C-CH_3,$$

the compounds are named as "16-(R,S)methyl-18,19-tetradehydro" compounds.

When —$C(L_1)R_7$ is —$CH_2CH=CH_2$ the compounds so described are named as "19,20-didehydro".

When at least one of $R_3$ and $R_4$ is not hydrogen then there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the carbacyclin analogs so represented contain as asymmetric carbon atom at C-14. Accordingly, two epimeric configurations are possible: "(16S)" and "(16R)". Further, there is described by this invention the C-16 epimeric mixture: "(16RS)".

When $X_1$ is —$CH_2OH$, the compounds so described are named as "2-decarboxy-2-hydroxymethyl" compounds.

When $X_1$ is —$CH_2NL_2L_3$, the compounds so described are named as "2-decarboxy-2-aminomethyl" or "2-(substituted amino)methyl" compounds.

When $X_1$ is —$COL_4$, the novel compounds herein are named as amides. Further, when $X_1$ is —$COOR_1$ and $R_1$ is other than hydrogen the novel compounds herein are named as esters and salts.

When $X_1$ is CN the novel compounds herein are named as 2-decarboxy-2-cyano compounds.

Examples of phenyl esters substituted in the para position (i.e., $X_1$ is —$COOR_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p(p-acetamidobenzoyloxy)phenyl ester, and p-hydroxybenzaldehyde semicarbazone ester.

Examples of novel amides herein (i.e., $X_1$ is —$COL_4$) include the following:

(1) Amides within the scope of alkylamino groups of the formula $NR_9R_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tertbutylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tertbutylcyclopentylamide, cyclohexylamide, 4-tertbutylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methy-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, o-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 2,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4- chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)-methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula $-NR_{53}COR_{51}$ are methylcarbonylamide, ethylcarbonylamide, phenylcarbonylamide, and benzylcarbonylamide.

(4) Amides within the scope of sulfonylamino of the formula $-NR_{53}SO_2R_{51}$ are methylsulfonylamide, ethylsufonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of $(C_3-C_{10})$ cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of $(C_7-C_{12})$ aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

The compounds of Formulas I and I(a) produce certain prostacyclin-like pharmacological responses. Accordingly, the novel formula I compounds are useful as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and as antithrombotic agents as indicated below.

(a) Platelet Aggregation Inhibition

The compounds of Formulas I and I(a) are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2-4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation the therapy. In vitro applications utilize a dose of 0.001–1.0 µg per ml of whole blood. The compounds of the present invention are useful in the treatment of peripheral vascular diseases, in the same manner as described in U.S. Pat. No. 4,103,026.

(b) Gastric Secretion Reduction

Compounds of Formulas I and I(a) are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 µg to about 20 µg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 0.001 to 100 mg per kg of body weight per day is employed. Once healing of the ulcers has been accomplished the maintenance dosage required to prevent recurrence is adjusted downward so long as the patient or animals remains asymptomatic.

The final products of specific Examples 6 and 7 contained herein demonstrate good cytoprotective properties with relatively low blood pressure effects in rats rendering said compounds preferred embodiments of the present invention.

(c) NOSAC-Induced Lesion Inhibition

Compounds of Formulas I and I(a) are also useful in reducing the undesirable gastrointestinal effects resulting from systemic administration of anti-inflammatory prostaglandin synthetase inhibitors, and are useful for that purpose by concomitant administration of said compounds of Formulas I and I(a) and the anti-inflammatory prostaglandin synthetase inhibitor. See Partridge, et al., U.S. Pat. No. 3,781,429, for a disclosure that the ulcerogenic effect induced by certain nonsteroidal anti-inflammatory agents in rats is inhibited by concomitant oral administration of certain prostaglandins of the E series. Accordingly these novel Formulas I and I(a) compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formulas I and I(a) are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formulas I and I(a) compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formulas I and I(a) compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When $X_1$ is —$COOR_1$, the novel Formula I and I(a) compounds so described are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula I and I(a) for the purposes described above are those with pharmacologically acceptable metal cations, ammonia, amine cations, or quaternary ammonium cations. Illustrative pharmacological acceptable cations which $R_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, $\alpha$-phenylethylamine, $\beta$-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris-(hydroxymethyl) aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When $X_1$ is —$CH_2NL_2L_3$, the Formula I and I(a) compounds so described are used for the purposes described in either free base or pharmacologically acceptable acid addition salt form.

The acid addition salts of the 2-decarboxy-2-aminomethyl- or 2-(substituted aminomethyl)- Formula I compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula I with the stoichiometric amount of the acid corresponding to the pharmacologically acceptable acid addition salt.

To obtain the optimum combination of biological response specificity, potency, and duration of activity, certain compounds within the scope of this invention are preferred. Preferred compounds of the present invention are Formula I compounds wherein $Z_4$ is —$CH_2$—, and of these compounds those wherein Y is —$CH_2CH_2$—, —$C\equiv C$— or trans —$CH=CH$— and/or $X_1$ is —$COOR_1$ are preferred especially when $R_1$ is hydrogen, methyl, ethyl, or a pharmacologically acceptable cation such as sodium. Compounds of Formula I wherein $R_7$ is cyclohexyl, n-pentyl or —$(CH_2)_3$—$CH=C(CH_3)_2$ are preferred. And compounds wherein $Y_1$ is —$SCH_2$— or $M_1$ is H,H or β-H,α-OH are also preferred.

In describing the preparation of the compounds of the present invention reference is made to Chart A to Chart K. In the Charts the various substituent groups have the following meanings. In Chart A: $R_7$, $L_{60}$, $Z_4$, $X_1$, $L_{20}$, $M_1$, and $L_1$ have the meanings defined in Formula I(a); alkyl is a hydrocarbon chain of from 1 to 4 carbon atoms and is straight or branched, e.g., methyl, ethyl, etc.; $Y_2$ is —$CH_2CH_2$— or —$SCH_2$—; $M_2$ is =O protected as a ketal, α-H:β-ORx, α-ORx:β-H, or H,H where Rx is a protecting group as defined below; $L_2$ is the same as $L_1$ in Formula I(a) only any hydroxyl groups are protected as ORx where Rx is as defined below; $L_{21}$ is the same as $L_{20}$ in Formula I(a) only $L_{21}$ is not =O and any hydroxy groups are protected as ORx where Rx is as defined below; $L_{22}$ is the same as $L_{20}$ in Formula I(a) only any hydroxyl groups are protected as ORx where Rx is as defined below; and $W_1$ has the meaning defined in Chart A. In Chart B: $W_2$ has the meaning defined in Chart B; $L_{60}$ and $R_7$ have the meanings defined in Formula I(a); $Y_3$ is —$CH_2CH_2$—; cis—CH=CH—, trans—CH=Ch— or —C≡C—; alkyl; $L_2$ and $L_{22}$ have the meanings defined above in Chart A; $M_3$ is α-H:β-OH or α-OH:β-H; $M_1$ is =O, α-H:β-ORx, α-ORx:β-H; Ra is the same as $R_7$ in Formula I(a) only Ra is not a group containing any unsaturation; Rb is an unsaturated group defined by $R_7$ in Formula I(a) wherein the double bond is protected by bromine or an epoxide group; Rc represents an unsaturated $R_7$ group; and Rd represents an unsaturated group of $R_7$ only the double bond is protected with an epoxide function. In Chart C: $L_{60}$ is as defined in Formula I and $L_{22}$ has the meaning defined in Chart A above. In Chart D: Ph is phenyl; $L_{60}$ has the meaning defined in Formula I(a); and $L_{21}$ is as defined in Chart A above. In Chart E: Ph is phenyl; $L_{60}$, $M_1$, $L_1$, $R_7$, $Z_4$ and $X_1$ have the meanings defined in Formula I(a); $Y_3$ has the meaning defined in Chart B; and $L_{22}$ has the meaning defined in Chart A above. In Chart F the groups $Y_2$, $L_2$, $M_2$ and $R_7$ have the meanings defined in Chart A and alkyl has from 1 to 4 carbon atoms.

During the preparation of the compounds of the present invention it may be necessary or desirable to protect the various hydroxyl groups at positions 11, 15, 16 or those contained in substituent $R_7$ as ORx groups where Rx is a suitable protecting group. Many suitable protecting groups are known in the art and are described, for example in U.S. Pat. No. 4,401,824, particularly column 11, line 21 through column 13, line 15, wherein such groups are described as is the manner of adding and removing such groups on the hydroxyl. The aforesaid portions of U.S. Pat. No. 4,401,824 are incorporated herein by reference. Although any of these protecting groups may be employed those preferred are tetrahydropyranyl (THP), tetrahydrofuran (THF), tert-butyldimethylsilyl and tert-butyldiphenylsilyl. It may be useful, of course, to use protecting groups which may be hydrolyzed selectively and also when group $R_7$ contains an hydroxyl to be protected generally this hydroxyl is protected using the same type of group that is used at positions C-11, C-15 or C-16.

The compounds of the present invention are prepared by various means utilizing 2,3,3A,4-tetrahydro-5-methoxy-2-oxo-naphtho[2,3-B]furan depicted as Formula II. Although in describing the preparation of the compounds of Formulas I and I(a) only one optical enantiomer may be depicted the processes are applicable to both the D and L optical isomers or mixtures thereof unless, of course, a particular step is steroselective. The compounds of Formula I(a) wherein $Y_1$ is —$CH_2CH_2$— or —$SCH_2$— are prepared as depicted in Chart A. The enollactone (II) is alkylated with two equivalents of a phosphonate anion (III) followed by one equivalent of acetic acid after which the reaction is warmed to effect the intramolecular Wadsworth-Emmons reaction, this procedure being an improved modification of the procedure of C. A. Henrick, et al., J. Am. Chem. Soc. 90, 5926 (1968). The resulting enone (IV) is reduced to the ketone (V) by procedures known in the art. For example the enone is hydrogenated over palladium catalyst in ethanol at 3 atmospheres pressure and may be followed by oxidation if necessary using, for example, Jones reagent. Equilibration to the thermodynamically favored ketone is achieved typically under basic conditions using, for example, potassium hydroxide in ethanol by procedures known in the art. When in compounds of Formula IV $R_7$ is a group containing a double bond such double bond is protected prior to reduction of the enone. For example the double bond can be protected by treatment of compound IV with one equivalent of bromine in carbon tetrachloride and following reduction of the enone and conversion to intermediate VI (see below) the double bond is deprotected by treatment of the ketone by heating with zinc in acetic acid or ethanol. Also the double bond can be protected by treatment of compound IV with meta-chloroperbenzoic acid (MCPBA) in methylene chloride to give an epoxide which can be removed, restoring the double bond following reduction of the enone and conversion (see below) to intermediate VI, by treatment with tri-n-butylphosphine with heating (see M. J. Boskin and D. B. Denney, Chem. Ind., London, 330, 1959) or treatment with tungsten hexachloride and lithium iodide with heating (see K. B. Sharpless, et. al., J. Am. Chem. Soc. 94, 6538 (1972)). The ketone (V) is then used to prepare compounds of Formula I(a) or the intermediates (VI) which are utilized in preparing compounds of Formula I(a).

To prepare intermediates (VI) wherein $L_{21}$ is α-H,β-OH, or α-OH,β-H the ketone (V) is reduced by procedures known in the art, for example using sodium borohydride. Conversion of the ketone (V) to the intermediate (VI) where $L_{21}$ is methylene, i.e., =$CH_2$, typically is achieved via a Wittig-type procedure, for example, using methylenetriphenylphosphorane by generally known procedures. Alternatively, the methylene group can be prepared by treatment of ketone (V) with the anion of methyl phenyl-N-methyl sulfoxime in tetrahydrofuran followed in a subsequent step by sulfoxime elimination with aluminum amalgam (see Aristoff, P. A. and Harrison, A. W., Tetrahedron Lett. 23, 2067–2070 (1982)). The methylene intermediate can be used to prepare compounds IX as depicted in Chart A or can be reduced to the corresponding compound wherein $L_{21}$ is α-$CH_3$,β-H, for example, via hydrogenation over palladium catalyst by procedures known in the art. The methylene intermediate can also be used to prepare the corresponding compound wherein $L_{21}$ is α-$CH_2OH$,β-H by hydroboration using, for example, borobicyclononane (9-BBN) followed by work-up with basic hydrogen peroxide. The intermediates of (VI) wherein $L_{21}$ and $L_{60}$ taken together form a double bond are prepared by treating the ketone (V) with a hydrazine derivative, such as, tosylhydrazine, followed by a Shapiro reaction on the resulting tosylhydrazone (see R. H. Shapiro, Chapter 3 in Organic Reactions, Volume 23, pp. 405–507). The 10,11-didehydro intermediate thus obtained can be used to prepare compounds (IX) as depicted in Chart A or can be hydrogenated, e.g., using palladium over charcoal, to intermediates (VI) wherein $L_{21}$ is H.H.

The compounds of (V) and (VI) are converted to the phenols (VII) by, for example, treatment with lithium diphenylphosphide in tetrahydrofuran as generally described by R. E. Ireland and D. M. Walba, Tetrahedron Letters, 1071 (1976). Other methods for aryl methyl ether cleavages are known and may be employed, e.g., see M. V. Bhatt and S. U. Kulkarni, Synthesis 249 (1983). The phenols are converted to compounds (VIII)(a) by selective alkylation, for example, using potassium carbonate and a nitrile of the formula Cl-$Z_4$-CN wherein $Z_4$ has the meaning defined in Formula I(a) by procedures generally known in the art. The phenols are converted to compounds (VIII)(b) by treatment with one equivalent of base, e.g., sodium hydride, and an appropriate halo alkanoate, e.g., alkyl bromo alkanoate of the formula Br$Z_4$-COOalkyl wherein alkyl has, e.g., from 1 to 4 carbon atoms and $Z_4$ has the meaning defined in Formula I(a). The compounds (VIII)(a) and (b) are hydrolyzed to the corresponding carboxylic acids of (VIII)(c) by procedures known in the art, for example, by using aqueous potassium hydroxide in methanol. The carboxylic acids of (VIII)(c) are converted to the final products (IX) wherein $X_1$ is COOH upon hydrolysis of any protecting groups at positions 11, 15 or 16 and the ketal protecting the C-15 is carbonyl. The carboxylic acids of (VIII)(c) can also be converted to compounds IX wherein $X_1$ is other than COOH by conventional means. For example, the carboxylic acid derivative can be reduced to (IX) wherein $X_1$ is —CH$_2$OH by treatment with lithium aluminum hydride. The thus formed C-1 alcohols, i.e., compounds IX wherein $X_1$ is CH$_2$OH can be oxidized to the corresponding carboxaldehyde which on treatment with a salt of hydroxylamine gives the oxime which is dehydrated to give the nitrile, i.e., compounds (IX) wherein $X_1$ is CN. The carboxylic acid derivative also can be converted to the various esters and amides defined in Formula I(a), and the amides can be reduced to the corresponding amines by using lithium aluminum hydride as generally described in U.S. Pat. No. 4,073,808. Following the conversions to the various $X_1$ groups any protecting groups present at C-11, C-15 or C-16 may be removed by hydrolysis as described hereinabove.

Compounds of Formula I(a) wherein $Y_1$ is other than —SCH$_2$— are prepared using the aldehyde depicted in Chart B as Formula XI. By the procedures generally described in Chart U of U.S. Pat. No. 4,306,075 the Formula XI aldehyde is reacted with an alkyl phosphonate of Formula X under the conditions of a Wittig reaction to give a ketone of Formula XII. The ketone can be used to prepare final products of Formula I(a) or can be reduced by hydride reduction to the trans-vinyl α- or β-alcohol, i.e., compounds of formula XIII wherein $M_3$ is α-OH,β-H or α-H,β-OH. The trans-vinyl alcohol of XIII can be used to prepare final products of Formula I(a) or when $R_7$ is other than a group containing unsaturation can be hydrogenated to give compounds of Formula XIV wherein Ra is $R_7$ except it is other than a group containing unsaturation. If prior to the initial reaction of the aldehyde of Formula XI and the phosphonate X any double bond present in the group $R_7$ is protected, as for example by treatment with one equivalent of bromine or by treatment with MCPBA as generally described hereinabove in connection with compounds of Formula IV in Chart A, the corresponding compounds of Formulas XII(a), XIII(a) and XIV(a) are obtained wherein Rb is one of the unsaturated groups of $R_7$ defined in Formula I(a) except that any unsaturation is protected by bromine or an epoxide function. Thus the compounds of Formula XIV(a) can be deprotected by treatment with zinc in acetic acid or ethanol when halogen protection is employed or by treatment with tributylphosphine or tungsten hexachloride and lithium iodide when epoxide protection is employed to give compounds of Formula XV wherein Rc is an $R_7$ unsaturated group as defined in Formula I(a). The compounds of Formulas XII and XIII wherein $R_7$ is other than a group containing unsaturation and of Formulas XII(a) and XIII(a) can be dihalogenated at C-13, C-14 and subsequently dehydrohalogenated by procedures well known in the art, e.g., see U.S. Pat. No. 4,029,681 or C. Gandolfi, et al., Il Farmaco, Ed. Sci. 27, 1125 (1972), to give compounds of Formula XVI wherein $R_7$ has the meaning defined in Formula I(a) and of Formula XVI(a) wherein Rd is

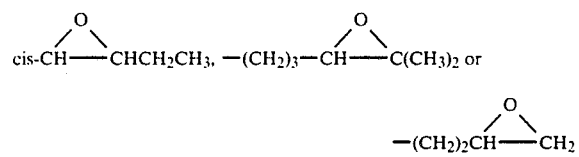

The compounds of Formula XVI can be used to prepare final products of Formula I(a) or the compounds of Formulas XVI and XVI(a) can be hydrogenated using a Lindlar catalyst to give the cis-vinyl alcohols of Formulas XVII and XVII(a) wherein $R_7$ and Rd are as defined above. The compounds of Formula XVII can be used to prepare final products of Formula I(a) or can be selectively oxidized to the cis-vinyl ketones of Formula XVIII using, e.g., DDQ or manganese dioxide, by procedures known in the art. The epoxides of Formula XVII(a) can be treated with tributylphosphine or tungsten hexachloride and lithium iodide as described hereinabove to remove the epoxide protecting groups. When $R_5$ in the $M_1$ substituent of Formula I(a) is methyl the appropriate starting materials are obtained by oxidizing the alcohols of Formulas XIV, XV and XVI to the corresponding ketones by procedures known in the art and then the resulting ketones as well as the vinyl ketones of Formulas XII and XVIII are treated with methyl lithium or a methyl Grignard by well known procedures. The compounds of Formulas XIII, XIV, XV, XVI and XVII wherein $M_3$ is α-H,β-OH or α-OH,β-H can be treated with a leaving group, e.g., converting the $M_3$ OH to OTs followed by a displacement reaction using, e.g., lithium aluminum hydride, to give the corresponding compounds wherein $M_3$ is H,H.

Collectively and for convenience all the starting materials prepared in connection with Chart B are depicted by Formula XIX in Chart B wherein $M_1$, $L_{60}$, and $R_7$ have the meanings defined in Formula I; $M_3$ is α-H,β-OH or α-OH,β-H;; and $L_2$ and $L_{22}$ are the same as $L_1$ and $L_{20}$ respectively in Formula I(a) only any hydroxyl group present is protected. The compounds of Formula XIX are converted to final products of Formula I(a) by the same procedures set forth in Chart A for converting compounds VI and V to compounds IX. Prior to making these conversions any hydroxyl groups at positions 11, 15, 16 or in the $R_7$ group can be protected as $ORx$ as described hereinabove.

The compounds of Formula XI are prepared as set forth in Chart C and Chart D. In Chart C the 2,3,3A,4-tetrahydro-5-methoxy-2-oxo-naphtho[2,3-B] furan (Formula II) is treated with the anion of trimethylphosphonoacetate followed by cyclization as generally described in connection with the reaction of compounds of Formulas II and III in Chart A. Alternatively the lactone (II) is treated at low temperature with the anion of methyl acetate (or ethyl acetate to give the ethyl ester analog) followed by warming to effect the cyclization. Compounds XX are reduced to the ketone XXI by means known in the art, e.g., by hydrogenation using palladium catalyst. The ketone XXI is reduced to the C-11 alcohol by, e.g., treatment with sodium borohydride after which the carboxy ester is reduced to the hydroxymethyl compound (XXII) using, e.g., excess diisobutylaluminum hydride. The compound of formula XXII is converted to the aldehyde of formula XI by procedures known in the art, e.g., by protection of the C-13 alcohol with an $ORx$ group followed by oxidation of the C-11 alcohol to the ketone, e.g., with Collins reagent, followed by conversion of the C-11 ketone to any of the $L_{22}$ groups as previously described, hydrolysis of the C-13 protecting group and oxidation to the aldehyde.

In Chart D the lactone II is alkylated with the anion of dimethylphosphonate in a manner similar to that described for the reaction of compounds II and III in Chart A. The enone of Formula XXIII is reduced, e.g., by hydrogenation at room temperature over palladium catalyst by procedures known in the art to give the ketone of Formula XXIV the ketone enolate of which is alkylated using benzylchloromethyl ether by procedures known in the art to give compounds of Formula XXV wherein Ph is phenyl. The ketones of Formula XXV are converted to the various C-11 analogs of Formula XXVI by the same general procedures described for the conversion of compounds V to compounds VI in Chart A. Any hydroxyl group present at the C-11 substituent is protected appropriately as described hereinbefore prior to proceeding to compounds of Formula XXVII. Cleavage of the benzyl ethers of Formula XXVI by hydrogenation, procedures known in the art, gives the 12-hydroxymethyl compounds of Formula XXVII which are oxidized to the aldehydes of Formula XI using Collins reagent by known procedures.

The compounds of Formula IV in Chart A can also be prepared as depicted in Chart F. The 2,2-ethylenedioxy-5-methoxynaphthalen-3-ylacetic acid (Formula XXXVI) is reacted with two equivalents of a phosphonate of Formula III as generally described in connection with the preparation of compounds of Formula IV in Chart A to give the compounds of Formula XXXVII. The Formula XXXVII compound is deketalized by means known in the art, e.g., by treatment with aqueous acid followed by reprotection of any hydroxyl groups in the $-C(M_2)C(L_2)R_7$ chain as generally described herein. The ketone of Formula XXXVIII is then treated with base, e.g., sodium hydride in glyme to give the enone of Formula IV.

Compounds of Formula I(a) wherein $Y_1$ is other than $-SCH_2-$ can also be prepared as depicted in Chart E. Compounds XXVIII are obtained as depicted in Chart D (see compounds XXV and XXVI) and are converted to the phenols of Formula XXIV by cleavage of the methyl ether using lithium diphenylphosphide in tetrahydrofuran as generally described hereinabove in connection with the preparation of compounds VII in Chart A. The phenols of Formula XXIX are converted to the compounds of XXX by the general procedures described in connection with the compounds of Formula VII to compounds of Formula IX in Chart A. The compounds of Formula XXX are converted to the aldehydes of Formula XXXIV by the general procedures described in connection with the preparation of compounds XI from compounds XXVI in Chart D, and the aldehydes of Formula XXXIV in turn are converted to the compounds of Formula XXXV by the general procedures described in Chart B for preparing compounds XIX.

Compounds of Formula I(a) also can be prepared as depicted in Chart E beginning with compounds of Formula XXXI which are obtained as described in Chart C (see Formulas XXI and XXII). Cleavage of the methyl ether of XXXI is accomplished using lithium diphenylphosphide in tetrahydrofuran as described hereinbefore followed by esterification, e.g., using diazomethane, and the resulting phenols (XXXII) are converted to the compounds of Formula XXXIII by the general procedures described in connection with the conversion of compounds VII to compounds IX in Chart A. The compounds of XXXIII are then converted to the corresponding aldehydes of XXXIV as generally described in Chart C (i.e., XXII to XI).

The compounds of Formula I(a) wherein

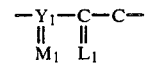

taken together is

are prepared by treating an aldehyde of Formula XXXIV (see Chart E) with a semicarbizide of the formula $H_2NNC(=O)NH-R_7$ by procedures known in the art. The semicarbazides are obtained by procedures generally known in the art by converting an $R_7CHO$ compound to the corresponding imine which is reduced to an amine. The amine is treated with dimethylcarbonate to give the corresponding carbamate which is treated with hydrazine hydrate to give the semicarbazide.

The phosphonates of Formulas III (Chart A) and X (Chart B) are known in the art or are prepared by procedures known in the art (see, for example, U.S. Pat. Nos. 4,029,681 and 4,401,824 and as depicted in Charts G. H and J.

In Chart G the cyclohexylcarboxaldehyde (1) is alkylated with vinyl Grignard or vinyl lithium to give the vinyl alcohol (5) by procedures known in the art. Kinetic resolution of the vinyl alcohol (5) to give compound (6) is accomplished by the method of Sharpless (Martin, V. S., et al., J. Am. Chem. Soc. 103, 6237 (1981). Alternatively, the cyclohexylcarboxyaldehyde is alkylated with acetylene anion by known procedures to give the ethynyl alcohol (2) which is oxidized to the ketone (3) using, e.g., Jones reagent, by known procedures. The ketone (3) is reduced assymetrically using chiral reagents by known procedures. See, e.g., Midland, M. M., J. Org. Chem. 47, 2815 (1982); J. Org. Chem. 46, 3933 (1981), and J. Am. Chem. Soc. 102, 867 (1980); and also, Cohen, N., J. Org. Chem. 45, 583 (1980) and Brinkmeyer, R. S., and Kapoor, V., J. Am. Chem. Soc. 99, 8339 (1977). The ethynyl alcohol (4) is then partially reduced using, e.g., sodium bis(2-methoxyethoxy)aluminum hydride in toluene or hydrogenation over Lindlar catalyst by known procedures. The vinyl alcohol (6) is then protected, e.g., as a tetrahydropyranyl group, and either subjected to iodoboration by the general procedures of H. C. Brown, "Organic Synthesis via Boranes," John Wiley, N.Y., 1975, pp. 101-102, to give compound (11) or is subjected to hydroboration and oxidation using, e.g., 9-borabicyclononane followed by alkaline peroxide work-up by known procedures to give 4-cyclohexyl-4-ORx-propanol. The propanol is converted to compound 11 by direct replacement of the primary OH with iodide using iodine and a triaryl phosphine as generally described by B. R. Castro, "Organic Reactions," 29, p. 1, ed., W. G. Dauben, John Wiley, N.Y., 1983. Alternatively the primary OH of the propanol is selectively activated, e.g., via tosylation followed by displacement of the tosylate with iodide in acetone and diisopropylamine to give compound (11). Compound (11) is treated with the anion of dialkyl methyl phosphonate to give compound (12).

As depicted in Chart G, the protected vinyl alcohol (7) may also be converted to the alcohol (8) by, e.g., ozonolysis and treatment with a reducing agent such as sodium borohydride. The alcohol (8) can be converted to the iodide (9) directly or via the tosylate as described above in connection with the preparation of compound (11). The iodide (9) is then alkylated with a dialkyl methylthio phosphonate following the general methods outlined by M. Mikolajczk, et al., J. Org. Chem. 44, 2967 (1979) to give compound (10). The alcohol (8) can also be obtained from D-mandelic acid (15) as depicted in Chart G by hydrogenating the acid over rhodium catalyst by known procedures, e.g., T. Hirano, et al., Makrmol. Chem. 177, 3237 (1976) to give α-hydroxycyclohexaneacetic acid (14) which is converted to the ester (13) by generally known procedures. The ester (13) is then reduced to give compound (8) using, e.g., excess diisobutylaluminum hyrdide. D-mandelic acid (15) can also be used to prepare compound (19) in Chart G. The hydroxyl group of the acid is protected using, e.g., as a tetrahydropyranyl group, then the acid is reduced to the alcohol, using, e.g., sodium bis(2-methoxyethoxy)aluminum hydride in toluene or using lithium aluminum hydride after which the alcohol is converted to the iodide (16) directly or via the tosylate in the manner generally described in connection with the preparation of compound (11). The iodide (16) is then alkylated using, e.g., vinyl Grignard or vinyl lithium with nickel or copper catalysis by generally known procedures to give the vinyl compund (17) which is converted to the iodide (18) in the same manner as described above for the conversion of compound (7) to compound (11). The iodide (18) is treated with trimethylphosphite under the conditions of an Arbuzov reaction to give the phosphonate (19).

In Chart H there is described additional means of obtaining phosphonates useful in preparing compounds of this invention. The acetylene (20) is partiallly reduced to the trans vinyl compound (21) using, e.g., sodium bis(2-methoxyethoxy)aluminum hyrdide by known procedures. The vinyl alcohol is subjected to Sharpless asymmetric epoxidation as generally described by B. E. Rossiter, et al., J. Am. Chem. Soc. 103, 464 (1981) and T. Katsuki and K. B. Sharpless, J. Am. Chem. Soc. 102, 5974 (1980) to give compound (22) which is reduced to the alcohol (23) by general procedures described by J. M. Finan and Y. Kishi, Tetrahedron Lett. 23, 2719 (1982). By selective activation the primary hydroxyl of compound (23) is tosylated to give (24), the tosylate of which is converted to the iodide using, e.g., sodium iodide to give compound (25). The secondary hydroxyl of compound (25) is protected and the compound is alkylated with the anion of dialkyl methylphosphonate to give compound (27) by general procedures known in the art.

Chart J also sets forth means for obtaining phosphonates for use in preparing the compounds of this invention. Alkylation of 4-bromo-2-methyl-2-butene, compound (28), is achieved with allyl magnesium bromide using, e.g., copper or nickel catalysis by known procedures to give compound (29) which is subjected to hydroboration and oxidation using, e.g., 9-borabicyclononane, followed by hydrogen peroxide workup to give the alcohol (30) which is converted to the iodide, compound (31) e.g., by the procedures described in connection with the preparation of compound (11) in Chart G. Alternatively compound (29) can be subjected to hydroboration and iodination to give compound (31) by known procedures. Compound (31) is then alkylated with the dianion of propargyl alcohol by known procedures to give compound (32) which is partially reduced to give 33, e.g., using sodium bis(2-methoxyethoxy)aluminum hydride, then converted to the phosphonate (34) by procedures generally described hereinabove.

Although Charts G, H, and J depict the preparation of specific phosphonates wherein $R_7$ is cyclohexyl, phenyl, alkyl or alkenyl, the methods there described are applicable generally to the phosphonates used herein.

The compound of Formula II is prepared as depicted in Chart K and as described in Example 1.

EXAMPLE 1

2,3,3A-4-Tetrahydro-5-methoxy-2-oxo-naphtho[2,3-B]furan (a)

3,4-Dihydro-2-hydroxy-5-methoxynaphthalenecarboxylic acid methyl ester (Chart K, Compound 35)

A solution of 5-methoxy-β-tetralone (20.6 g, 117 mmol) and 350 ml of dimethylcarbonate was cooled to 0° to 5°, then treated with 32 ml (140 mmol) of 25 sodium methoxide in oxygen-free methanol. The resulting dark brown solution was stirred for 30 minutes at 0°, then heated to 70°, stirred for 18 hours under a nitrogen atmosphere, then cooled to 0° to 5° and quenched with 200 ml of cold 1N degassed aqueous hydrochloric acid. The solution was extracted with ethyl acetate (2×150 ml). The combined organic layers were washed with brine (2×200 ml), dried over magnesium sulfate, filtered, and rotary evaporated at 50°. The resulting red-brown oil was crystallized from 80 ml of 1:1 ether/hexane in the freezer to give 14.43 g (53%) of yellow crystals, m.p. 56°-58°. A second crop of yellow crystals (3.6 g, 14%) can be obtained from 20 ml 1:1 ether/hexane, m.p. 55°-58°. The mother liquor (~12 g) was chromatographed on 100 g of silica gel 60 slurry packed in 300 ml of hexane. Eluting with 2% ethyl acetate in hexane gave 5.1 g (19%) of the title compound (a) in fractions 17–28, m.p. 53°–58°. Total yield of compound (a) was 23.1 g (85%).

NMR (CDCl$_3$, TMS): δ 2.3–2.7 (m, 2H), 2.8–3.0 (m, 2H), 3.80 (s, 3H), 3.90 (s, 3H), 6.6–7.5 (m, 3H), 13.35 (s, 1H).

Infrared: ν$_{max}$ (mull): 1640, 1598, 1587, 1566, 1422, 1378, 1311, 1277, 1220, 1207, 1086, 1052, 1030, 892, 787, 769, 721 cm$^{-1}$.

TLC (Silica Gel GF): RF=0.47 in 10% ethyl acetate in hexane.

(b) 3,4-Dihydro-2-hydroxy-3-(3-propene)-5methoxy naphthalenecarboxylic acid methyl ester (Chart K, Compound 36)

A solution of 300 ml of tetrahydrofuran and 39 ml (282 mmol) of diisopropylamine under nitrogen, was cooled to −50° C. and treated with 170 ml (272 mmol) of 1.6M n-butyllithium in hexane dropwise maintaining the temperature at −50° C. The solution was stirred at −50° for 15 minutes, then at 0° for 15 minutes. A solution of 30.0 g (128.1 mmol) of 3,4-dihydro-2-hydroxy-5-methoxynaphthalenecarboxylic acid methyl ester in 70 ml of tetrahydrofuran was added dropwise to maintain the temperature at 0°. The resulting yellow suspension was treated with 13.5 ml (160 mmol) of allyl bromide in 50 ml of tetrahydrofuran dropwise maintaining the temperature at 0°. The cooling bath was removed and the orange solution was stirred at ambient temperature for 1 hour, then cooled to 10° to 15° C. and 500 ml of 1N degassed aqueous hydrochloric acid was added dropwise maintaining the temperature below 15°. The layers were separated and the aqueous layer extracted with 400 ml of ethyl acetate. The organic layers were combined and washed with 500 ml of brine, dried over anhydrous magnesium sulfate, filtered and concentrated via rotary evaporation and then house vacuum to give 44.2 g of the title compound (b), m.p. 70°–71°.

NMR (CDCl$_3$, TMS): δ1.8–3.2 (m, 5H), (3H singlets at 3.80 δ and 3.90 δ; 6H) 4.7–5.4 (m, 2H), 5.5∝6.1 (m, 1H), 6.5–7.6 (m, 3H), 13.4 (s, 1H).

Infrared: ν$_{max}$ 2925, 2956, 1237, 1598, 1440, 1270, 1257, 1051, 1002, 885, 790, 772 cm$^{-1}$.

TLC (Silica Gel GF): Rf=0.34 in 10% ethyl acetate in hexane.

(c) 1,2,3,4-Tetrahydro-5-methoxy-3-(3-propene)naphthalen-2-one (Chart K, Compound 37)

A mixture of 44.1 g of 3,4-dihydro-2-hydroxy-5-methoxy-3-(3-propene)naphthalenecarboxylic acid methyl ester and 110 ml of dimethyl sulfoxide was degassed with nitrogen and heated to ∼50° under nitrogen to effect dissolution. The resulting orange solution was treated with 6.0 g (142 mmol) of anhydrous lithium chloride and 7.5 ml of deionized water and heated to 150° under nitrogen, then stirred at 150° for 4 hours. The solution was cooled to 10° to 15°, diluted with 500 ml of 1:1 brine/water and extracted with three 200 ml portions of ethyl acetate. The organic layers were combined and washed with three 200 ml portions of water, two 200 ml portions of brine, dried over anhydrous magnesium sulfate, filtered and concentrated in vacuo to give 28.3 g of the title compound (c), m.p. 39°–40°.

NMR (CDCl$_3$, TMS): δ 1.8–2.8 (m, 4H), 3.0–4.3 (m, including 2H broad singlet at 3.53 δ and 3H singlet at 3.80 δ, 6H), 4.8–5.4 (m, 2H), 5.5–6.1 (m, 1H), 6.5–7.4 (m, 3H).

Infrared: ν$_{max}$ 2922, 1713, 1642, 1599, 1588, 1472, 1441, 1436, 1258, 1081, 910, 771, 719, 609 cm$^{-1}$.

TLC (Silica Gel GF): Rf=0.32 in 10% ethyl acetate in hexane.

(d) The 2-ethylenedioxy ketal of 1,2,3,4-tetrahydro-5-methoxy-3-(3-propene)naphthalen-2-one (Chart K, Compound 38)

A solution of 27.8 g (128 mmol) of 1,2,3,4-tetrahydro-5-methoxy-3-(3-propene)naphthalen-2-one, 450 ml of methylene chloride, 150 ml (2.2 mmol) of ethylene glycol, 60 ml (450 mmol) of triethylorthoformate, and 270 mg (1.41 mmol) of p-toluenesulfonic acid monohydrate was degassed with nitrogen and stirred at room temperature under nitrogen for 22 hours after which the reaction was quenched with 7.5 ml (52 mmol) of triethylamine, diluted with 500 ml of 1:1 saturated aqueous sodium bicarbonate/water and the layers were separated. The aqueous layer was extracted with 200 ml of methylene chloride. The combined organic layers were washed with three 500 ml portions of water and 500 ml of brine, then concentrated by rotary evaporation to give ∼40 g of a red oil. The red oil was dissolved in 200 ml of hexane and treated with 200 ml of water. The mixture was degassed and stirred under nitrogen for one hour. The layers were separated and the organic layer was dried with anhydrous magnesium sulfate, then filtered and concentrated in vacuo to give ∼35 g of an orange oil. The orange oil was filtered through 100 g of silica gel 50 washing with 800 ml of 10% ethyl acetate in hexane. The filtrate was concentrated in vacuo to give 31.5 g (94%) of the title compound (d), m.p. 34°–35°.

NMR (CDCl$_3$, TMS)"δ 1.7–3.3 (m, including 2H broad singlet at 2.90 δ, 7H), 3.4–4.4 (m, including 3H singlet at 3.77 δ, 7H), 4.8–5.3 (m, 2H), 5.6–6.2 (m, 1H), 6.5–7.4 (m, 3H).

Infrared: ν$_{max}$ (film): 2940, 2890, 1620, 1590, 1470, 1440, 1260, 1155, 1075, 950, 770 cm$^{-1}$.

TLC (Silica Gel GF): Rf=0.35 in 10% ethyl acetate in hexane.

(e) 2,2-Ethylenedioxy-5-methoxy-1,2,3,4-tetrahydro-naphthalen-3-ylacetic acid (Chart K, Compound 39)

To a mixture of 1400 ml of deionized water and 66.5 g (310 mmol) of sodium metaperiodate was added 1.0 g (6.4 mmol) of potassium permanganate. The purple solution was stirred for 30 minutes at room temperature then treated in sequence with 5.0 g (36 mmol) of anhydrous potassium carbonate, then 350 ml of t-butanol, followed by 8.9 g (34 mmol) of the ethylenedioxy ketal of 1,2,3,4-tetrahydro-5-methoxy-3-(3-propene)naphthalen-2-one in 350 ml of t-butanol. The resulting reddish-purple suspension was stirred at room temperature for 2 hours. The reaction was quenched with 10 ml (150 mmol) of ethylene glycol and stored at room temperature for 2.5 hours. Approximately 30% of the solvent was removed via rotary evaporation, and the remaining material was acidified to pH 3–4 with 100 ml of 1M aqueous hydrochloric acid and extracted with three 500 ml portions of ethyl acetate. The organic layers were combined and washed with two 500 ml portions of brine, dried over anhydrous sodium sulfate, filtered, and the solvents removed in vacuo to give 8.5 g (89%) of the title compound (e), m.p. 129°–130°.

Infrared: ν$_{max}$ 2927, 1703, 1587, 1471, 1266, 1143, 1082, 1059, 948, 873, 765 cm$^{-1}$.

NMR (CDCl$_3$, TMS): δ 1.8–3.4 (m, 6H), 3.9–4.5 (m, including 3H singlet at 3.77 δ, 8H), 6.4–7.4 (m, 3H), 10.27 broad singlet, 1H).

TLC (Silica Gel GF): Rf=0.20 in 30% ethyl acetate in hexane.

(f)
5-Methoxy-2-oxo-1,2,3,4-tetrahydronaphthalen-3-ylacetic acid (Chart K, Compound 40)

A solution of 8.0 g (28.7 mmol) of 2,2-ethylenedioxy-5-methoxy-1,2,3,4-tetrahydronaphthalen-3-ylacetic acid, 80 ml of 3N aqueous hydrochloric acid, and 80 ml of acetone was degassed and heated to 60° under nitrogen then stirred under nitrogen at 60° for 4 hours. The reaction was cooled to room temperature, approximately 50% of the solvent was removed by rotary evaporation, diluted with 100 ml of brine, and extracted with three 100 ml portions of ethyl acetate. The organic layers were combined and washed with two 100 ml portions of brine, dried over anhydrous sodium sulfate, filtered, and concentrated via rotary evaporation to give an orange solid. The orange solid was triturated with 10 ml of ether and filtered to give 4.9 g (73%) of the title compond (f), m.p. 129°–131°.

NMR (CDCl$_3$, TMS): δ 2.2–3.2 (m, 4H), 3.3–4.0 (m, including 2H broad singlet at 3.67 δ and 3H singlet at 3.85 δ, 6H), 6.4–6.9 (m, 2H), 7.1–7.3 (m, 1H), 10.2 (bs, 1H).

Infrared: $\nu_{max}$ 2908, 2855, 1730, 1714, 1676, 1471, 1454, 1446, 1266, 1202, 1195, 1184, 1091, 776, 747, 724, cm$^{-1}$.

TLC (Silica Gel GF): Rf=0.22 in 35% ethyl acetate in hexane with 1% acetic acid.

(g)
2,3,3A,4-Tetrahydro-5-methoxy-2-oxo-naphtho[2,3-B]furan (Chart K, Compound 41)

A solution of 5-methoxy-2-oxo-1,2,3,4-tetrahydronaphthalen-3-yl-acetic acid (1.75 g, 7.49 mmol) in 88 ml of ethyl acetate was treated all at once with 88 ml of a reagent prepared immediately before use as follows: 20.0 ml of a solution of 0.40 ml of 70% perchloric acid in 100 ml of ethyl acetate was added to 50 ml of ethyl acetate, then 19.2 ml (0.20 mmol) of acetic anhydride was added and the reagent diluted to a total volume of 100 ml with ethyl acetate. The solution was stirred for 10 minutes at room temperature under nitrogen then quenched with 100 ml of saturated aqueous sodium bicarbonate. The layers were separated and the organic layer was washed with 100 ml of brine, dried with anhydrous sodium sulfate, filtered and concentrated in vacuo. To remove the excess acetic anhydride, the red oil was treated with 10 drops of pyridine and 200 ml of methanol. The solvents were removed in vacuo (rotovap bath below 30°); then to remove the pyridine 100 ml of toluene was added and the solvents were removed in vacuo (rotovap bath below 35°). An additional 100 ml of toluene was added and concentrated in vacuo to give a yellow solid. The yellow solid was recrystallized from ethyl acetate and hexane to give 890 mg (55%) of the title compound (g) as a white solid, m.p. 139°–141°.

NMR (CDCl$_3$, TMS): δ 2.0–4.1 (m, including 3H singlet at 3.86 δ, 8H), 6.0–6.2 (d, J=3 Hz, 1H), 6.6–7.0 (m, 2H), 7.0–7.4 (m, 1H).

Infrared: $\nu_{max}$ 2926, 1800, 1686, 1571, 1472, 1444, 1267, 1075, 964, 865, 850, 780 cm$^{-1}$.

CMR (CDCl$_3$, TMS): δ ppm (relative intensity): 173.94 (14), 156.31 (17), 154.89 (18), 134.98 (17), 127.79 (92), 121.42 (11), 119.48 (90), 109.60 (97), 101.09 (81), 55.48 (64), 34.76 (88), 33.17 (88), 27.29 (85).

UV: 218 nm (ε=17,650), 267 nm (ε=7,150), 293 nm (sh, ε=2,000), 303 nm (sh, ε=1,150).

TLC (Silica Gel GF): Rf=0.32 in 15% ethyl acetate in hexane.

EXAMPLE 2

Dimethyl[(4S)-tetrahydropyran-2-yloxy-nonyl]phosphonate

(a) 2-Octen-1-ol (Chart H, Compound 21)

A solution of 200 ml of dry tetrahydrofuran, degassed with nitrogen and cooled to 0° to 5°, and 85 ml (289 mmol) of 3.4M solution of sodium bis(2-methoxyethoxy) aluminum hydride in toluene was treated with 30.0 g (238 mmol) of 2-octyn-1-ol in 200 ml of dry tetrahydrofuran dropwise over one hour maintaining the temperature at 0° to 5°. The solution was removed from the cooling bath and stirred at ambient temperature for 3 hours then cooled to below −20° and carefully quenched (vigorous evolution of hydrogen occurs) with 1M aqueous sulfuric acid (∼10 ml) until the evolution of gas ceases. The quenched reaction mixture was poured into 1 L of cold 1M aqueous sulfuric acid, the layers separated, and the aqueous layer extracted with three 300 ml portions of ethyl acetate. The organic layers were combined and washed with 400 ml of brine, dried over anhydrous sodium sulfate, filtered, and concentrated in vacuo to give 30.4 (100%) of the title compound (a) which was distilled at 60° at 1 mm Hg to provide an analytical sample.

NMR (CDCl$_3$, TMS): δ 0.9 (t, J=6 Hz, 3H), 1.1–1.8 (m, 6H), 1.8–2.2 (m, 2H), 2.97 (s, 1H), 4.0–4.2 (m, 2H), 5.6–5.8 (m, 2H).

CMR (CDCl$_3$, TMS): δ 133.38, 129.00, 63.69, 32.24, 31.45, 28.90, 22.56, 14.02.

Infrared: $\nu_{max}$ (film) 3331, 2927, 2858, 1671, 1468, 1379, 1089, 1001, 969 cm$^{-1}$.

TLC (Silica Gel GF): Rf=0.26 in 10% ethyl acetate in hexane (the plate was developed twice).

(b) 2,3-Epoxyoctan-1-ol (Chart H, Compound 22)

To 2.0 L of methylene chloride, degassed with nitrogen and cooled to −20° under nitrogen, was added 70.8 ml (238 mmol) of titanium (IV) isopropoxide followed by 44.8 ml (262 mmol) of (+)-diethyl-L-tartrate maintaining the temperature below −15°. The mixture was stirred for 10 minutes. A solution of 30.4 g (240 mmol) of 2-octen-1-ol was added in 30 ml of methylene chloride dropwise maintaining the temperature below −15°. An additional 10 ml of methylene chloride was added and the solution stired for 10 minutes after which 104 ml (480 mmol) of t-butylhydroperoxide (4.6M in 1,2-dichloroethane) was added dropwise maintaining the temperature below −15°. The reaction solution was stirred for 24 hours at −20°. The pale yellow reaction solution was cannulated using nitrogen pressure into a 0° to 5° solution of 1400 ml of deionized water containing 400 g of ferrous sulfate and 200 g of d-tartaric acid vigorously stirred. The yellow-green emulsion was stirred for 30 minutes at ambient temperature then filtered through celite, the layers separated, and the aqueous layer extracted with two 500 ml portions of methylene chloride which had been used to wash the filter cake. The organic layers were combined, dried over anhydrous sodium sulfate, filtered, and concentrated in vacuo to give a colorless oil. The oil was dissolved in 600 ml of hexane and 300 ml of t-butylmethyl ether, degassed with nitrogen, and cooled to 0° under nitrogen after which the solution was treated with 500 ml of ice cold 1N aqueous sodium hydroxide and vigorously stirred for 30 minutes under nitrogen at 0°. The aqueous layer was saturated with sodium chloride. The layers were separated and the aqueous layer extracted with two 150 ml portions of 2:1 hexane/t-butylmethyl ether. The organic layers were combined, washed with two 300 ml portions of brine, dried over anhydrous sodium sulfate, filtered, and concentrated in vacuo to give ~25 g of colorless oil. The oil was chromatographed on 300 g of silica gel 60 eluting with 20% ethyl acetate in hexane to give (57%) of the title compound (b).

NMR (CDCl$_3$, TMS): $\delta$ 0.9 (t, J=6 Hz, 3H), 1.0–2.1 (m, 8H), 2.6–3.2 (m, 3H), 3.4–4.2 (m, 2H).

CMR (CDCl$_3$, TMS): 67 62.08, 58.90, 56.26, 31.67, 25.69, 22.61, 13.97.

Infrared: $\nu_{max}$ (mull) 3115, 2961, 2854, 1584, 1037, 1008, 991, 877, 730 cm$^{-1}$.

TLC (Silica Gel GF): Rf=0.19 in 30% ethyl acetate in hexane.

Specific Rotation: $[\alpha]_D = -35°$ (95% ethanol).

(c) 1,3-Octandiol (Chart H, Compound 23)

To a solution of 250 ml of dry tetrahydrofuran, degassed with nitrogen and cooled to 0° to 5° under nitrogen, and 46.0 ml (156 mmol) of 3.4M solutions of sodium bis(2-methoxyethoxy) aluminum hydride in toluene was added 15.0 g (104 mmol) of 2,3-epoxyethan-1-ol in 120 ml of dry tetrahydrofuran dropwise over one hour. An additional 10 ml of dry tetrahydrofuran was added and the mixture was stirred at 0° to 5° for 16 hours. The reaction solution was then quenched at 0° to 5° with 10 ml of 1M aqueous sulfuric acid, and the resulting white slurry was poured into 1 L of ice cold 1M aqueous sulfuric acid. The layers were separated and the aqueous layer was extracted with three 250 ml portions of ethyl acetate. The organic layers were combined, washed with 250 ml of saturated aqueous sodium bicarbonate and 250 ml of brine, dried over anhydrous sodium sulfate, filtered and concentrated in vacuo to give 14.4 g (95%) of the title comoound (c).

NMR (CDCl$_3$, TMS): $\delta$ 0.9 (t, J=6 Hz, 3H), 1.0–1.8 (m, 10H), 3.2–4.0 (m, 5H).

Infrared: $\nu_{max}$ (film): 3345, 2872, 2860, 1468, 1460, 1379, 1130, 1056 cm$^{-1}$.

TLC (Silica Gel GF): Rf=0.30 in 70% ethyl acetate in hexane.

Specific Rotation: $[\alpha]_D = +8°$ (in 95% ethanol).

(d) 2-(p-Toluenesulfonyloxy)octan-3-ol (Chart H, Compound 24)

A solution of 14.2 g (97.1 mmol) of 1,3-octandiol and 200 ml of dry pyridine degassed with nitrogen and cooled to 0° was treated with 19.4 g (102 mmol) of p-toluenesulfonyl chloride and stirred for 18 hours at 0° under nitrogen. The reaction mixture was then poured onto 500 g of ice and stirred until the ice dissolved. The mixture was extracted with three 200 ml portions of ethyl acetate. The organic layers were combined, washed with 200 ml of brine, dried over anhydrous sodium sulfate, filtered and concentrated in vacuo at room temperature using two 200 ml portions of toluene to azeotropically remove the pyridine to give 24.5 g (84%) of the title compound (d).

NMR (CDCl$_3$, TMS): $\delta$ 0.9 (t, J=6 Hz, 3H), 1.0–2.2 [m, including broad singlet (1H) at 2.1 11H], 2.43 (s, 3H), 3.5–3.9 (m, 1H), 4.0–4.4 (m, 2H), 7.4 (d, J=9 Hz, 2H), 7.75 (d, J=9 Hz, 2H).

Infrared: $\nu_{max}$ (film) 3545, 3432, 2955, 2930, 2859, 1598, 1358, 1189, 1176, 1097, 958, 911, 814, 665 cm$^{-1}$.

TLC (Silica Gel GF): Rf=0.5 in 50% ethyl acetate in hexane.

(e) 1-Iodooctan-3-ol (Chart H, Compound 25)

A solution of 24.5 g of 1-(p-toluenesulfonyloxy)octan-3-ol and 75 g (500 mmol) of sodium iodide was degassed with nitrogen and heated to 50° under nitrogen, then stirred at 50° for one hour. The suspension was cooled to 25° and most of the acetone was removed in vacuo at room temperature. The resulting red-orange solid was dissolved with 500 ml of ethyl acetate and 500 m of 1:1 brine/water. The layers were separated and the aqueous layer extracted with 100 ml of ethyl acetate. The organic layers were combined, washed with 100 ml of 5% aqueous sodium thiosulfate, 200 ml of brine, and dried over anhydrous sodium sulfate, filtered and concentrated in vacuo to give 19.84 g of title compound (e).

(f) 1-Iodooctan-3-ol, 0-tetrahydropyranyloxy (Chart H, Compound 26)

A solution of 19.84 g of 1-iodooctan-3-ol and 100 ml of methylene chloride, degassed with nitrogen, was combined with 15 ml (150 mmol) of dihydropyran and 100 mg of pyridine hydrochloride and then stirred at room temperature under nitrogen for 18 hours. The reaction solution was washed with 100 ml of saturated aqueous sodium bicarbonate, 100 ml of brine, dried over anhydrous sodium sulfate, filtered and concentrated in vacuo. The crude product was chromatographed on 300 g of silica gel 60 slurry packed with hexane, eluting with 3% ethyl acetate in hexane to give 11.47 g of the title compound (f).

NMR (CDCl$_3$, TMS): $\delta$ 0.9 (t, J=6 Hz, 3H), 1.1–2.3 (m, 16H), 3.0–4.1 (m, 5H), 4.8 (bs, 1H).

Infrared: $\nu_{max}$ (film) 2932, 2858, 1465, 1455, 1440, 1209, 1200, 1132, 1077, 1024, 871 cm$^{-1}$.

TLC (Silica Gel GF): Rf=0.40 in 5% ethyl acetate in hexane.

(g) Dimethyl[(4S)-tetrahydropyran-2-yloxynonyl]phosphonate (Chart H, Compound 27)

To 300 ml of dry tetrahydrofuran, degassed with nitrogen and cooled to $-40°$ under nitrogen, was added 6.0 ml (57.5 mmol) of diethylamine. The solution was treated with 34.0 ml (52.7 mmol) of n-butyllithium (1.55M in hexane) dropwise maintaining the temperature below $-30°$ and stirred at $-35°$ to $-30°$ for 15 minutes, then cooled to $-75°$. A solution of 6.54 g (52.7 mmol) of dimethylmethylphosphonate in 50 ml of dry tetrahydrofuran was added dropwise maintaining the temperature below $-70°$. Stirring was continued for 30 minutes at $-75°$ to $-70°$ after which 16.31 g (47.9 mmol) of 1-iodooctan-3-ol, 0-tetrahydropyranyloxy in 100 ml of dry tetrahydrofuran was added dropwise maintaining the temperature below $-70°$. The mixture was stirred at $-70°$ for one hour and the reaction mixture allowed to warm to $-10°$ over 4 to 5 hours. The mixture was carefully quenched with 500 ml of 1:1 brine/water and extracted with two 400 ml portions of ethyl acetate. The organic layers were combined, washed with 500 ml of brine, dried over anhydrous sodium sulfate, filtered and concentrated in vacuo to give a crude product which was chromatographed on 300 g of silica gel 60 slurry packed in ethyl acetate. The product was eluted with 1 L of ethyl acetate followed by 2 L of 15% acetone in ethyl acetate to give 11.47 g of the title compound (g).

NMR (CDCl$_3$, TMS): δ 0.9 (t, J=6 Hz, 3H), 1.1–2.1 (m, 20H), 3.3–4.1 (m, including two 3H singlets at 3.70 and 3.80, 9H), 4.67 (bs, 1H).

Infrared: $\nu_{max}$ (film) 2952, 1464, 1456, 1246, 1200, 1183, 1133, 1076, 1062, 1030, 995, 831, 813 cm$^{-1}$.

TLC (Silica Gel GF): Rf=0.24 in ethyl acetate.

EXAMPLE 3

9-Deoxy-13,14-dihydro-2',9α-methano-3-oxa-4,5,6-trinor-3,7-(1',3-interphenylene)-PGF$_1$ (a)
8,12-Didehydro-9,11-dideoxy-13,14-dihydro-2',9α-methano-3-oxa-11-oxo-1,4,5,6-tetranor-3,7-(1',3'-interphenylene)-PGF$_1$, 15-(tetrahydropyranyl ether)

A solution of 11.90 g (35.37 mmol) of dimethyl[(4S)-tetrahydropyran-2-yloxynonyl]phosphonate and 450 ml of dry tetrahydrofuran, degassed and flushed with nitrogen, was cooled to −78° C. The stirred solution was treated with 22.5 ml (36.0 mmol) of 1.60M n-butyllithium dropwise over 15 to 20 minutes then stirred for one hour at −78° C. A solution of 3.71 g (17.17 mmol) of 2,3,3A,4-tetrahydro-5-methoxy-2-oxo-naptho[2,3-B]furan in 70 ml of dry tetrahydrofuran, degassed and flushed with nitrogen and cooled to −78° C. under nitrogen, was added via cannula and under nitrogen pressure dropwise over 30 minutes. The resulting solution was stirred for 4 hours while allowing the temperature to rise slowly to −10° after which the solution was treated dropwise with 1.03 ml (18 mmol) of glacial acetic acid. The reaction mixture was stirred for 15 minutes at ambient temperature and heated at 60° to 65° for 6 hours. The resulting yellow-green solution was cooled to 5°, neutralized to about pH 6 to 7 with 500 ml of brine containing 18 ml (18 mmol) of 1M aqueous hydrochloric acid, and extracted with three 250 ml portions of ethyl acetate. The organic layers were combined and washed with 200 ml of 3:1 brine/saturated aqueous sodium bicarbonate and then with 400 ml of brine and dried over anhydrous sodium sulfate, filtered and concentrated in vacuo. The resulting crude product was chromatographed on 200 g of silica gel 60 degassed with nitrogen eluting with 1 L of 20% ethyl acetate in hexane. The elution was continued with 1 L of ethyl acetate followed by 2 L of 25% acetone in ethyl acetate to give 4.96 g (68%) of title compound 3(a).

NMR (CDCl$_3$, TMS): δ 0.9 (t, J=6 Hz, 3H), 1.0–3.1 (m, 22H), 3.3–4.2 (m, including 3H singlet at 3.83 δ, 9H), 4.63 (bs, 1H), 6.6–7.3 (m, 3H).

Infrared $\nu_{max}$ (film): 1700, 1652, 1584, 1471, 1456, 1439, 1268, 1252, 1133, 1091, 1077, 1032, 771 cm$^{-1}$.

UV (95% ethanol): λ nm ($\epsilon_{max}$) 229 (17,050), 272 (3,500), 281 (3,150).

TLC (Silica Gel GF): Rf 0.26 in 20% ethyl acetate in hexane.

(b) 9,11-DIDEOXY-13,14-DIHYDRO-2',9∇-METHANO-3-oxa-11-oxo-1,4,5,6-tetranor-3,7-(1',3'-interphenylene)-12-epi-PGF$_1$, 15-(tetrahydropyranyl ether)

To a solution of 4.95 G (11.6 mmol) of the compound of Example 3(a) in 250 ml of degassed absolute ethanol was added a solution of 1.67 g of 10% palladium on carbon and 112 mg (0.81 mmol) of anhydrous potassium carbonate. The resulting mixture was hydrogenated at 50 psi (3.4 atm) for 42 hours after which the mixture was filtered through a pad of 1:1 celite/anhydrous magnesium sulfate. The filter cake was washed with two 200 ml portions of ethyl acetate. The colorless solution was concentrated in vacuo using 200 ml of toluene to azeotrope the last traces of water and ethanol to give 5.2 g of colorless oil. [TLC(Silica gel GF; 20% ethyl acetate in hexane): 2 spots (neither visible under UV light) Rf=0.28 and 0.38.] The colorless oil was dissolved in 65 ml of acetone then degassed and flushed with nitrogen and cooled to −40° to −35° C. The solution was treated dropwise with 4.78 ml (12.8 mmol) of Jones Reagent over 10 to 15 minutes and stirred at −40° to −35° for 2 hours under nitrogen. The excess Jones Reagent was quenched with 3.1 ml (40 mmol) of 2-propanol at −40° to 35° and the mixture was stirred for 30 minutes after which 3 g of solid sodium bicarbonate was added. The mixture was stirred for 15 minutes at ambient temperature after which the green suspension was filtered through celite and the filter cake was washed with four 70 ml portions of ethyl acetate. The combined filtrates were washed with two 100 ml portions of saturated aqueous sodium bicarbonate and 100 ml of brine. The aqueous washes were combined and back extracted with 100 ml of ethyl acetate. The organic layers were combined, dried over anhydrous sodium sulfate, filtered, and concentrated in vacuo. The resulting dark brown oil was filtered through 20 g of silica gel 60 washing with 500 ml of 20% ethyl acetate in hexane. The filtrate was concentrated in vacuo to give 4.7 g (95%) of compound 3(b) as a pale brown oil.

NMR (CDCl$_3$, TMS): δ 0.9 (t, J=6 Hz, 3H), 1.0–4.2 (m, including 3H singlet at 3.83 ppm, 33H), 4.6 (bs, 1H), 6.6–6.9 (m, 2H), 6.9–7.3 (m, 1H).

TLC (Silica Gel GF): Rf=0.38 in 20% ethyl acetate in hexane.

(c)
9,11-Dideoxy-13,14-dihydro-2',9α-methano-3-oxa-11-oxo-1,4,5,6-tetranor-3,7-(1',3'-interphenylene)-PGF$_1$, 15-(tetrahydropyranyl ether)

To 4.7 g (10.9 mmol) of the compound of Example 3(b) in 450 ml of 95% ethanol was added 90 ml of 10% aqueous sodium hydroxide and the resulting solution was degassed and flushed with nitrogen and heated at reflux (bath temperature 105°) for 7.5 hours under nitrogen. The reaction was cooled to room temperature and approximately two-thirds of the solvent was removed in vacuo at room temperature and the remaining material was diluted with 500 ml of brine and extracted with three 200 ml portions of ethyl acetate. The combined organics were washed with 200 ml of brine, dried over anhydrous sodium sulfate, filtered and concentrated in vacuo. The crude product was flash chromatographed on 240 g of silica gel (230–400 mesh ASTM) eluting with 10% ethyl acetate in hexane collecting 200 ml fractions to give 4.41 g (94%) of the title compound 3(b) as a colorless oil.

NMR (CDCl$_3$, TMS): δ 0.9 (t, J=6 Hz, 3H), 1.0–4.2 (m, including 3H singlet at 3.83 ppm, 33H), 4.6 (bs, 1H), 6.6–6.9 (m, 2H), 6.9–7.3 (m, 1H).

Infrared $\nu_{max}$ (film): 1738, 1588, 1469, 1440, 1257, 1200, 1133, 1113, 1091, 1077, 1050, 1032, 1023, 993, 769 cm$^{-1}$.

TLC (Silica Gel GF): Rf=0.41 in 20% ethyl acetate in hexane.

(d)
9-Deoxy-13,14-dihydro-2',9α-methano-3-oxa-1,4,5,6-tetranor-3,7-(1',3'-interphenylene)-PGF$_1$ To 2.80 g (74.0 mmol) of sodium borohydride, degassed and flushed with nitrogen, and cooled to −30°, was slowly added 350 ml of absolute methanol and the resulting material was stirred for 10 minutes and treated with a solution of 10.2 g (23.8 mmol) of the compound of Example 3(c) in 15 ml of dry methylene chloride and 76 ml of absolute methanol dropwise maintaining the temperature of the solution at −30°. The resulting solution was stirred at −30° for 4 hours, then at −25° for 2.5 hours after which the reaction was quenched with 19.0 ml of glacial acetic acid then diluted with 600 ml of brine and extracted with four 250 ml portions of ethyl acetate. The organic layers were combined and washed with 300 ml of saturated aqueous sodium bicarbonate, then washed with 300 ml of brine, dried over anhydrous sodium sulfate, filtered and concentrated in vacuo to give 10.1 g of a colorless oil [TLC(Silica gel GF; 20% ethyl acetate in hexane): 5 spots with the major spot at $R_f=0.20$.] The oil was dissolved in 60 ml of tetrahydrofuran and diluted with 180 ml of glacial acetic acid and 90 ml of deionized water, degassed and flushed with nitrogen, and stirred at 40° to 45° under nitrogen for 3 hours. The solution was then cooled to room temperature, diluted with 500 ml of brine and extracted with three 250 ml portions of 3:2 ethyl acetate/hexane. The organic layers were combined and washed with four 300 ml portions of brine. The aqueous layers were combined and back extracted with two 250 ml portions of 3:2 ethyl acetate/hexane. All the organic layers were combined, dried over anhydrous sodium sulfate, filtered and concentrated in vacuo using two 300 ml portions of toluene to azeotrope the acetic acid. The resulting colorless oil was chromatographed on 700 g of silica gel 60 eluting with 40% ethyl acetate in hexane to give 5.28 g (64%) of the title compound 3(d).

NMR (CDCl$_3$, TMS): δ 0.9 (t, J=6 Hz, 3H), 1.0–3.1 (m, including 2H singlet at 2.30 δ, 23H), 3.5–3.9 (m, including 3H singlet at 3.83 δ, 5H), 6.6–6.9 (m, 2H), 7.0–7.3 (m, 1H).

TLC (Silica Gel GF): R$_f$ 0.25 in 50% ethyl acetate in hexane.

Infrared: ν$_{max}$ (film): 3343, 1587, 1477, 1472, 1461, 1455, 1441, 1341, 1327, 1263, 1104, 1077, 1034, 734 cm$^{-1}$.

(e)
9-Deoxy-13,14-dihydro-2',9α-methano-3-oxa-1,4,5,6-pentanor-3,7-(1',3'-interphenylene)-PGF$_1$ A solution of 250 ml of dry tetrahydrofuran and 8.3 ml (47.7 mmol) of diphenylphosphine, degassed and cooled to 0° to 5° C. under introgen, was treated with 30.0 ml (46.5 mmol) of n-butyllithium (1.55M in hexane) dropwise over 15 minutes then stirred an additional 30 minutes at ambient temperature after which 5.6 g (16.2 mmol) of the compound of Example 3(d) in 50 ml of dry tetrahydrofuran was added under nitrogen pressure over 15 minutes. An additional two 10 ml portions of tetrahydrofuran were added and the mixture was heated at reflux for 8 hours under nitrogen. The solution was cooled to 0° to 5° C. after which 11.0 ml (63.6 mmol) of diphenylphosphine was added, then treated with 41.0 ml (63.6 mmol) of n-butyllithium (1.55M in hexane) dropwise over 10 to 15 minutes. The solution was stirred at ambient temperature for 30 minutes then refluxed for 16 hours all under nitrogen pressure. The solution was then cooled to 0° to 5° C. and poured into 465 ml of ice cold brine containing 125 ml of 1N aqueous hydrochloric acid (pH 3-4) and extracted with three 200 ml portions of ethyl acetate. The organic layers were combined, washed with 200 ml of brine, dried over anhydrous sodium sulfate, filtered, and concentrated in vacuo. The resulting colorless oil was chromatographed on 400 g of silica gel 60 eluting with 50% ethyl acetate in hexane to give the product.

NMR (CDCl$_3$, TMS): δ 0.9 (t, J=6 Hz, 3H), 1.0–3.0 (m, 21H), 3.3–3.9 (m, 2H), 4.4 (bs, 3H), 6.5–7.1 (m, 3H).

Infrared: ν$_{max}$ (film): 3345, 1590, 1465, 1280, 775 cm$^{-1}$.

TLC (Silica Gel GF): R$_f$=0.18 in 50/5 ethyl acetate in hexane.

(f)
2-Decarboxy-2-cyano-9-deoxy-13,14-dihydro-2',9α-methano-3-oxa-4,5,6-trinor-3,7-(1',3'-interphenylene)-PGF$_1$ The phenol from 3(e) (5.12 g, 15.4 mmol) was combined with 22.8 g (165 mmol) of anhydrous potassium carbonate, and 17.8 ml (281 mmol) of chloroacetylnitrile and 150 ml of acetone. The solution was degassed and flushed with nitrogen and refluxed for 24 hours under nitrogen and cooled to 15° to 20° C., diluted with 200 ml of 1:1 brine/water and extracted with 600 ml of ethyl acetate. The organic layer was washed with 200 ml of brine. The aqueous layers were combined and extracted with 200 ml of ethyl acetate. The organic layers were combined, dried over anhydrous sodium sulfate, filtered and concentrated in vacuo. The resulting oil was chromatographed on 400 g of silica gel 60 eluting with 20% acetone in methylene chloride to give the product.

NMR (CDCl$_3$, TMS): δ 0.9 (t, J=6 Hz, 3H), 1.0–3.0 (m, 21H), 3.20 (bs, 2H), 3.4–3.9 (m, 2H), 4.73 (s, 2H), 6.7–7.3 (m, 3H).

Infrared: ν$_{max}$ (film): 3360, 1610, 1585, 1470, 1455, 1415, 1265, 1235, 1105, 1080, 1040, 770, 740, 735 cm$^{-1}$.

TLC (Silica Gel GF): R$_f$ 0.26 in 20% acetone in methylene chloride.

(g) The nitrile from 3(f) (4.9 g, 13.2 mmol) was combined with 100 ml (445 mmol) of 25% aqueous potassium hydroxide, degassed and flushed with nitrogen. The solution was refluxed for 6 hours, cooled to 0° to 5°, acidified to pH 6 with 400 ml of ice cold 1N aqueous hydrochloric acid in 1 L of brine, and extracted with four 300 ml portions of ethyl acetate. The combined organic layers were washed with 500 ml of brine, dried over anhydrous sodium sulfate, filtered, and concentrated in vacuo. The resulting pink to red solid was chromatographed on 400 g of CC-4 acid washed silica gel eluting with 2 L of 50% ethyl acetate in hexane followed by 3 L of 70% ethyl acetate in hexane to give 5.10 g of solid which was crystallized from hot tetrahydrofuran and hexane to give 1.20 g of 9-deoxy-13,14-dihydro2',9α-methano-3-oxa-4,5,6-trinor-3,7-(1',3-interphenylene)-PGF$_1$ (m.p. 122°–124° C.).

NMR

(CD$_3$CCD$_3$, TMS):

δ0.9 (t, J=6 Hz, 3H), 1.0–3.1 (m, 21H), 3.3–3.9 (m, 2H), 4.3–5.3 (m including 2Hs at δ 4.67, 5H), 6.6–7.2 (m, 3H).

Specfic Rotation: $[\alpha]_D + 34°$ (c 0.901, 95% etOH).

Infrared: $\nu_{max}$ (mull): 3440, 3380, 2720, 2670, 2580, 1740 (weak), 1710, 1610, 1585, 1425, 1260, 1145, 1120, 1090, 1025 cm$^{-1}$.

EXAMPLE 4

Dimethyl [(4R)-4-cyclohexyl-4-tetrahydropyran-2-yloxybutyl]-phosphonate (a) 1-Cyclohexylprop-2-enol (Chart G, Compound 5)

To 140 ml of dry tetrahydrofuran, degassed and flushed with nitrogen (3×) and cooled to 0° C. under nitrogen, was added 1.3M vinyl magnesium bromide (195 ml, 253.5 mmol) in tetrahydrofuran rapidly and dropwise over 5 minutes. The resulting solution was stirred for 5 minutes at 0° C. under nitrogen after which a solution of 24.0 g (223 mmol) of cyclohexylcarboxaldehyde in 40 ml of dry tetrahydrofuran was added via syringe at 0° C. The resulting mixture was stirred for 3.75 hours at 0° to 5° C. under a nitrogen atmosphere after which the reaction was quenched at 0° C. by careful addition of saturated aqueous ammonium chloride. The resulting suspension was poured into 1 L of ice cold, saturated, aqueous ammonium chloride and extracted with three 600 ml portions of ethyl acetate. The ethyl acetate extracts were combined and washed with 1 L of saturated aqueous ammonium chloride, 1 L of saturated aqueous sodium bicarbonate, then twice with 1 L each of brine. The ethyl acetate extract was dried thoroughly over magnesium sulfate, filtered, and concentrated at room temperature via rotovap to give 31.0 g of 1-cyclohexylprop-2-enol.

NMR (CDCl$_3$, TMS): δ 0.73–2.67 (m, 12H, CH$_2$, CH), 3.87 (t, 1H, CH—O, J=6 Hz), 5.07–5.43 (m, 2H, CH=), 5.67–6.13 (m, 1H, CH=).

Infrared (film): 3370, 2925, 1450, 1020, 990, 975, 890 cm$^{-1}$.

TLC (Silica Gel GF): R$_f$=0.54 in 25% ethyl acetate in hexane.

(b) (R)-1-Cyclohexylprop-2-enol (Chart G, Compound 6)

To 2.2 L of methylene chloride, degassed and flushed with nitrogen and cooled to −25° C. under nitrogen, was added 72.2 ml of titanium tetraisopropoxide (242.5 mmol) at −25° C. under nitrogen. The solution was stirred for 3 to 5 minutes at −25° C. after which 62.16 ml of (−)-diisopropyl(D)tartrate (290 mmol) was added at −25° C. under nitrogen. A solution of 31.0 g (214 mmol) of 1-cyclohexylprop-2-enol in 50 ml of methylene chloride was added to the reaction mixture at −25° C. under nitrogen. The resulting solution was stirred for 5–10 minutes at −25° C. under nitrogen after which 3M t-butylhydroperoxide in dichloroethane (48.5 ml, 145.5 mmol) was added at −25° C. under nitrogen. The mixture was stirred for 10 minutes at −25° to −20° C. under nitrogen, then stirred for 3 days at −20° C. The reaction was quenched by cannulating the reaction mixture (at −20° C.) into a mechanically stirred tartaric acid-ferrous sulfate solution (200 g/400 g in 2 L water) at 0° C. The resulting suspension was stirred at 0° C. for 20 to 30 minutes and filtered through a pad of celite, washing the pad thoroughly with methylene chloride. The filtrate layers were separated and the aqueous layer was extracted with methylene chloride (2×500 ml each). The organic extracts were combined and washed with brine (2×1000 ml each), dried over magnesium sulfate, filtered and concentrated at room temperature via rotovap to give the title compound 4(b) as a yellow oil which was purified as follows: The oil was dissolved in 650 ml of hexane and cooled to 0° C. under nitrogen then treated with aqueous 1N sodium hydroxide (550 ml) at 0° C. under nitrogen. The resulting suspension was stirred for 40 minutes at 0° C. under nitrogen after which the layers were separated and the aqueous layer was extracted with hexane (2×500 ml each). The organic extracts were combined, washed with brine (500 ml), dried over sodium sulfate, filtered and concentrated at room temperature via rotovap to a yellow oil. The yellow oil was chromatographed on silica gel (1200 g) packed with 10% ethyl acetate in Skellysolve B (SSB) eluting with 12% in SSB to give 9.59 g of the title compound 4(b).

NMR (CDCl$_3$, TMS): δ 0.73–2.67 (m, 12H, CH$_2$, CH), 3.87 (ε, 1H, CH—O), 5.07–5.43 (m, 2H, CH=), 5.67–6.13 (m, 1H, CH=).

Infrared (film): 3370, 2925, 1450, 1020, 990, 975, 890 cm$^{-1}$.

TLC (Silica Gel GF): R$_f$=0.54 in 25% ethyl acetate in hexane.

(c) 3-Cyclohexyl-3-tetrahydropyranyloxy-prop-1-ene (Chart G, Compound 7)

A solution of 22.07 g of (R)-1-cyclohexylprop-2-enol in 300 ml of methylene chloride, degassed and washed with nitrogen, was treated at ambient temperature under nitrogen with pyridinehydrochloride (0.145 g) and then with dihydropyran (44.4 ml, 466 mmol). The reaction mixture was stirred overnight at ambient temperature under nitrogen, then cooled using an ice bath and treated with aqueous sodium bicarbonate (15 ml). The resulting solution was diluted with saturated aqueous sodium bicarbonate (200 ml), stirred for 5 minutes after which the layers were permitted to separate. The organic layer was washed with 200 ml of brine, dried over anhydrous sodium sulfate, filtered and the filtrate concentrated via rotovap to give 35.0 g of compound 4(c) as a yellow oil.

NMR (CDCl$_3$, TMS): δ 0.63–2.20 (m, 17H, CH$_2$, CH), 3.27–4.10 (m, 3H, CH—O, CH$_2$O), 4.67 (bs, 1H, CH—O, THP), 4.93–5.33 (m, 2H, CH=), 5.40–6.13 (m, 1H, CH=).

Infrared (film): 2925, 2855, 1130, 1115, 1080, 1035, 1020, 1015, 995, 980 cm$^{-1}$.

TLC (Silica Gel GF): R$_f$=0.62 in 25% ethyl acetate in hexane.

(d) 3-Cyclohexyl-3-tetrahydropyranyloxypropanol (Chart G, Compound 8)

A solution of 35.0 g of 3-cyclohexyl-3-tetrahydropyranolprop-1-ene (157 mmol) in 795 ml of dry tetrahydrofuran, degassed and flushed with nitrogen, then cooled to 0° C., was treated dropwise at 0° C. with 0.5M 9-BBN in tetrahydrofuran (795 ml, 398 mmol). The resulting solution was stirred for one hour at 0° C. after which the cooling bath was removed and stirring was continued at ambient temperature for 6 hours. The reaction mixture was then cooled to 0° C. and treated slowly with 30% hydrogen peroxide (231 ml), then treated with 3N potassium hydroxide (231 ml) all at once. The resulting suspension was stirred for 35 minutes at 0° C. after which the cooling bath was removed and the reaction suspension was stirred for one hour at ambient temperature. The reaction mixture was then diluted with brine (1 L), the layers separated and the aqueous layer was extracted with three 700 ml portions of ethyl acetate. The organic layers were combined and washed with three 500 ml portions of brine, dried over anhydrous sodium sulfate, filtered and the filtrate concentrated in vacuo at ~25° C. The resulting product was chromatographed on silica gel (1750 g) packed with 5% ethyl acetate in SSB, eluting with 8 L of 5% ethyl acetate in SSB, 6 L of 10% ethyl acetate in SSB, 6 L of 20% ethyl acetate in SSB, 6 L of 25% ethyl acetate in SSB, and 4 L of 30% ethyl acetate in SSB to give 27.19 g of compound 4(d).

NMR (CDCl$_3$, TMS): δ 0.63–2.90 (m, 20H, CH$_2$, CH, C—OH), 3.23–4.13 (m, 5H, CH—O, CH$_2$—O), 4.03–4.87 (m, 1H, CH—O, THP).

Infrared (film): 3435, 2930, 2855, 1450, 1160, 1135, 1075, 1025, 990 cm$^{-1}$.

TLC (Silica Gel GF): R$_f$=0.21–0.38 in 30% ethyl acetate in hexane.

(e) The 1-p-toluenesulfonyl derivative of 3-cyclohexyl-3-tetrahydropyranyloxypropanol A solution of 27.19 g (112 mmol) of 3-cyclohexyl-3-tetrahydropyranyloxypropanol in 136 ml of dry pyridine, degassed with nitrogen and cooled to 0° C., was treated with 25.7 g (135 mmol) of p-toluenesulfonyl chloride. The reaction mixture was stirred for 20 hours at 0° C. under nitrogen after which 350 g of ice was added and the cooling bath was removed. The reaction mixture was stirred for 75 minutes, then diluted with 600 ml of water, and extracted with three 500 ml portions of ethyl acetate. The organic layers were combined, washed with 600 ml of saturated aqueous sodium bicarbonate, 600 ml of water, and 600 ml of brine, and dried over anhydrous sodium sulfate, filtered and the filtrate concentrated via rotovap at room temperature. The residual pyridine was removed azeotropically at room temperature via rotovap using two 300 ml portions of toluene to give 38.09 g of compound 4(e).

NMR (CDCl$_3$, TMS): δ 0.63–2.20 (m, 19H, CH$_2$, CH), 2.47 (s, 3H, ArCH$_3$), 3.23–4.40 (m, 5H, CH—O, CH$_2$—O), 4.47 (m, 1, CH—O, THP), 7.37 (D, 2H, ArH; J=10, 5 Hz), 7.87 (D, 2H, ArH; J=10, 5 Hz).

Infrared (film): 2930, 2860, 1600, 1445, 1375, 1175, 905, 815, 670 cm$^{-1}$.

TLC (Silica Gel GF): R$_f$=0.48 in 20% ethyl acetate in hexane.

(f) (1-Tetrahydropyranyloxy-3-iodopropyl)cyclohexane (Chart G, Compound 11)

A solution of 36.74 g (92.65 mmol) of the compound from Example 4(e), 1.5 ml of diisopropylethylamine, 360 ml of acetone and 83.33 g (550 mmol) of sodium iodide was stirred at room temperature under nitrogen for 20 hours. The solution was then cooled using an ice bath and concentrated via rotovap at room temperature to give a red-orange solid. The solid was dissolved in 1L of ethyl of ethyl acetate. The organic layers were washed with 525 ml of 5% aqueous sodium thiosulfate then with 1 L of brine, dried over anhydrous magnesium sulfate, filtered and the filtrate concentrated via rotovap at room temperature to give a yellow oil. The oil was chromatographed on 900 g of silica gel packed with SSB, eluting with 4 L of SSB, then with 3% ethyl acetate in SSB to give 27.47 g of compound 4(f).

NMR (CDCl$_3$, TMS): δ 0.63–2.53 (m, 19H, CH$_2$, CH), 3.07–3.70 (m, 4H, CH$_2$—O, CH$_2$—I), 3.77–4.10 (m, 1H, CH—O), 4.48–4.82 (m, 1H, CH—O, THP).

Infrared (film): 2925, 2850, 1450, 1200, 1130, 1115, 1075, 1065, 1035, 1023, 980 cm$^{-1}$.

TLC (Silica Gel GF): R$_f$=0.47 in 10% ethyl acetate in hexane.

(g) [(4R)-4-Cyclohexyl-4-tetrahydropyran-2-yloxybutyl]-phosphonate (Chart G, Compound 12)

To 500 ml of dry tetrahydrofuran cooled to −40° C. under nitrogen was added 9.98 ml (96.7 mmol) of diethylamine. The solution was treated with 60 ml (93 mmol) of n-butyllithium (1.55M in hexane) dropwise maintaining the temperature below −30° C. The solution was stirred at −35° to −30° C. for 15 minutes then cooled to −75° C. A solution of 10.6 g (85.4 mmol) of dimethylmethyl phosphonate in 50 ml of dry tetrahydrofuran was added dropwise maintaining the temperature below −70° C. The solution was stirred for 30 minutes at −75° to −70° C. after which 27.29 g (77.5 mmol) of (1-tetrahydropyranyloxy-3-iodopropyl)cyclohexane in 100 ml of dry tetrahydrofuran was added dropwise maintaining the temperature below −70° C. The reaction mixture was stirred at −70° C. for one hour then allowed to warm to −10° C. over 4 hours. The reaction was quenched with 800 ml of 1:1 brine/water and the layers separated. The aqueous layer was extracted with two 650 ml portions of ethyl acetate. The organic layers were combined, washed with 800 ml of brine, dried over anhydrous sodium sulfate, filtered and the filtrate concentrated in vacuo. The resulting product was chromatographed on 500 g of silica gel packed with ethyl acetate eluting the product with 2 L of ethyl acetate and then with 6 L of 5% acetone in ethyl acetate to give 18.14 g of compound 4(g).

NMR (CDCl$_3$, TMS): δ 0.63–2.53 (m, 23H), 3.23–4.20 (m, 3H), 3.70 (s, 3H), 3.83 (s, 3H), 4.60 (bs, 1H).

Infrared (film): 2930, 3850, 1450, 1245, 1200, 1130, 1115, 1060, 1030, 990, 835, 815 cm$^{-1}$.

TLC (Silica Gel GF): Rf=0.14 in ethyl acetate.

EXAMPLE 5

15-Cyclohexyl-9,11-dideoxy-13,14-dihydro-2′, 9α-methano-11α-methyl-4,5,6,16,17,18,19,20-octanor-3,7-(1′,3′-interphenylene)-PGF$_1$ (Formula I where X$_1$ is CO$_2$H, Z$_4$ is CH$_2$, L$_{60}$ is H, L$_{20}$ is α-CH$_3$,β-H, Y$_1$ is CH$_2$CH$_2$, M$_1$ is α-OH,β-H and

is cyclohexyl (a) 15-Cyclohexyl-8,12-didehydro-9,11-dideoxy-13,14-dihydro-2′,9a-methano-3-oxa-11-oxo-1,4,5,6,16,17,18,19,20-nonanor-3,7-(1′,3′-interphenylene)-PGF$_1$, 15-(tetrahydropyranyl ether)

A solution of 11.9·g (35.37) mmol of the product of Example 4 and 450 ml of dry tetrahydrofuran, degassed and flushed with nitrogen, was cooled to −78° C. The stirred solution was treated with 22.5 ml (36.0 mmol) of 1.60M n-butyllithium dropwise over 15 to 20 minutes, then stirred for one hour at −78° C. A solution of 3.71 g (17.17 mmol) of 2,3,3A,4-tetrahydro-5-methoxy-2-oxo-naphtho[2,3-B]furan in 70 ml of dry tetrahydrofuran, degassed and flushed with nitrogen and cooled to −78° C. under nitrogen, was added via cannula and under nitrogen pressure dropwise over 30 minutes. The resulting solution was stirred for 4 hours while allowing the temperature to rise slowly to −10° C. after which the solution was treated dropwise with 1.03 ml (18 mmol) of glacial acetic acid. The reaction mixture was stirred for 15 minutes at ambient temperature and heated at 60° to 65° for 6 hours. The resulting yellow-green solution was cooled to 5°, neutralized to about pH 6 to 7 with 500 ml of brine containing 18 ml (18 mmol) of 1M aqueous hydrochloric acid, and extracted with three 250 ml portions of ethyl acetate. The organic layers were combined and washed with 200 ml of 3:1 brine/saturated aqueous sodium bicarbonate and then with 400 ml of brine and dried over anhydrous sodium sulfate, filtered and concentrated in vacuo. The resulting crude product was chromatographed on 200 g of silica gel to give the title compound 5(a).

(b)
15-Cyclohexyl-9,11-dideoxy-13,14-dihydro-2′,9a-methano-3-oxa-11-oxo-1,4,5,6,16,17,18,19,20-nonanor-3,7-(1′,3′-interphenylene)-12-epi-PGF$_1$, 15-(tetrahydropyranyl ether)

To a solution of 4.95 g of the compound of Example 5(a) in 250 ml of degassed ethanol was added a solution of 1.67 g (1.56 g/atom) of 10% palladium on carbon and 112 mg (0.81 mmol) of anhydrous potassium carbonate. The resulting mixture was hydrogenated at 50 psi 93.4 atm) for 42 hours after which the mixture was filtered through a pad of 1:1 celite/anhydrous magnesium sulfate (30 g). The filter cake was washed with two 200 ml portions of ethyl acetate. The colorless solution was concentrated in vacuo using 200 ml of toluene to azeotrope the last traces of water and ethanol to give 5.2 g of colorless oil which was filtered through 20 g of silica gel 60 washing with 500 ml of 20% ethyl acetate in hexane to give compound 5(b).

(c) 15-Cyclohexyl-9,11-dideoxy-13,14-dihydro-2′,9a-methano-3-oxa-11-oxo-1,4,5,6,16,17,18,19,20-nonanor-3,7-(1′,3′-interphenylene)-PGF$_1$, 15-(tetrahydropyranyl ether)

To 4.7 g of the compound of Example 5(b) in 450 ml of 95% ethanol was added 90 ml of 10% aqueous sodium hydroxide and the resulting solution was degassed and flushed with nitrogen and heated at reflux (bath temperature 105° ) for 7.5 hours under nitrogen. The reaction was cooled to room temperature and approximately two-thirds of the solvent was removed in vacuo at room temperature and the remaining material was diluted with 500 ml of brine and extracted with three 200 ml portions of ethyl acetate. The combined organics were washed with 200 ml of brine, dried over anhydrous sodium sulfate, filtered and concentrated in vacuo. The crude product was flash chromatographed on silica gel to give the title compound 5(c).

(d)
(15R)-15-Cyclohexyl-9,11-dideoxy-13,14-dihydro-2′,9a-methano-11-methylene-1,4,5,6,16,17,18,19,20-nonanor-3-oxa-3,7-(1′,3′-interphenylene)-PGF$_1$, 15-(tetrahydropyranyl ether)

A degassed solution of methyl phenyl-N-methyl sulfoxmine (1.502 g, 8.88 mmol) in freshly distilled tetrahydrofuran (26.6 ml) was cooled to −78° C. under nitrogen and treated dropwise with 2.9M methylmagnesium chloride in tetrahydrofuran (3.06 ml, 8.88 mmol). The resulting solution was stirred for 35 minutes at −78° C. and for 15 minutes at 0° C., cooled to −78° C. and treated with a solution of the product 5(c) (1.92 g, 4.36 mmol) in freshly distilled tetrahydrofuran (10 ml). Residual ketone starting material was transferred to the reaction with two 4 ml aliquots of freshly distilled tetrahydrofuran. The reaction was stirred for 1.75 hours while the temperature was permitted to go from −78° C. to 0° C., then was stirred for 2 hours at 0° C. The reaction was diluted with ice-cold brine (80 ml) and extracted with diethyl ether (3×110 ml). The ether extracts were washed with brine (80 ml), 0.2M aqueous potassium bisulfate (80 ml), aqueous saturated sodium bicarbonate (80 ml) and brine (80 ml), dried over magnesium sulfate, filtered and concentrated in vacuo to a yellow oil (3.49 g).

A degassed solution of the crude sulfoximine (3.37 g; theory 2.65 g) in freshly distilled tetrahydrofuran (66) was cooled to 0° C. under nitrogen and treated with 50% acetic acid/water (20 ml), followed immediately by aluminum amalgam which had been prepared by washing 20 mesh aluminum powder (3.55 g) with ether (75.5 ml) methanol (2×75.5 ml) then 3.57 g of mercuric chloride in water (122 ml) followed by methanol (75.5 ml) and ether (75.5 ml).

The resulting black suspension was permitted to stir for 2.75 hours while the reaction temperature was allowed to go slowly from 0° C. to 10° C., cooled to 0° C., diluted with ethyl acetate (100 ml) and stirred for 30 minutes at 0° C. The suspension was filtered through celite, and the filtercake was washed with ethyl acetate. The combined filtrate was washed with brine (135 ml) 0.2M aqueous potassium bisulfate (135 ml) and brine (135 ml), dried over sodium sulfate, filtered and concentrated to a yellow oil.

The crude product was chromatographed on silica gel in 5% ethyl acetate in hexane NMR (CDCl$_3$, TMS): δ 0.73–3.10 (m, 30), 3.27–3.63 (m, 2), 3.77–4.23 (m, 1), 3.80 (S, 3), 4.53–4.73 (m), 4.77–4.97 (m, 2), 6.63–6.90 (m, 2), 7.13 (d of d, 1, J$_1$=J$_2$=7.5 Hz).

Infrared (film): 2930, 2860, 1652, 1605, 1595, 1475, 1455, 1405, 1260, 1240, 1205, 1135, 1115, 1095, 1080, 1028, 995, 865, 768 cm$^{-1}$.

TLC (Silica Gel GF): Rf=0.58 in 1% ethyl acetate in hexane.

(e)
15-Cyclohexyl-9,11-dideoxy-13,14-dihydro-2′,9a-methano-11-methyl-1,4,5,6,16,17,18,19,20-nonanor-3-oxa-3,7-(interphenylene)-PGF$_1$, 15-tetrahydropyranyl ether A degassed solution of the product of 5(d) (0.156 g, 0.36 mmol) in absolute ethanol (11.15 ml) was treated at room temperature under nitrogen with 10% palladium on charcoal (0.052 g) and anhydrous potassium carbonate (0.06 g). The resulting suspension was alterntely degassed and flushed with nitrogen then degassed and flushed with hydrogen and hydrogenated at 50 p.s.i. for 22 hours. The suspension was evacuated and flushed with nitrogen, filtered through 1:1 celite/magnesium sulfate (3 g). The filtercake was washed with ethyl acetate and the combined filtrate was concentrated in vacuo to give 0.155 g of the title compound (e) as a crude oil.

NMR (CDCl$_3$, TMS): δ 0.70–3.21 (m, including doublet, 3, CH$_3$ at 0.90, J=6 Hz), 3.27–3.70 (m, 2), 3.80–4.30

(m, 1), 3.83, (s, 3), 4.60–4.90 (m, 1), 6.70–7.03 (m, 2), 7.13 (d of d, 1, $J_1=J_2=7.5$ Hz).

TLC (Silica Gel GF): Rf=0.58 in 10% ethyl acetate/hexane.

(f)

15-Cyclohexyl-9,11-dideoxy-13,14-dihydro-2′,9α-methano-11-methyl-1,4,5,6,16,17,18,19,20-nonanor-3-oxa-3,7-(1′,3′-interphenylene)-PGF$_1$ The crude product of example 5(e) in 8 ml of 4:2:2 acetic acid/water/tetrahydrofuran was stirred at 45° C. under nitrogen for 3 hours, cooled, diluted with brine and extracted with ethyl acetate. The organics were washed with brine, dried over sodium sulfate, filtered and concentrated to a yellow oil.

The crude product was chromatographed on silica gel in 10% ethyl acetate in hexane to give 0.116 g (90%) of the title compound (f).

NMR (CDCl$_3$, TMS): δ 0.07–3.03 (m, 29, including doublet, 3, J=6 Hz), 3.20–3.53 (m, 1), 3.83 (s, 3), 6.63–6.97 (m, 2), 7.13 (d of d, 1, $J_1=J_2=7.5$ Hz).

Infrared (film): 3370, 2930, 2850, 1605, 1595, 1475, 1444, 1375, 1330, 1310, 1260, 1100, 1080, 1045, 970, 895, 775, 735 cm$^{-1}$.

TLC (Silica Gel GF): Rf=0.51 in 25% ethyl acetate in hexane.

(g)

15-Cyclohexyl-1,2,4,5,6,16,17,18,19,20-decanor-9,11-dideoxy-13,14-dihydro-2′,9α-methano-11-methyl-3-oxa-3,7-(1′,3′-interphenylene)-PGF$_1$ A degassed solution of diphenylphosphine (0.173 ml, 0.973 mmol), in freshly distilled tetrahydrofuran (5.5 ml) was cooled to 0° C under nitrogen and treated with 1.58M n-butyllithium (0.60 ml, 0.95 mmol). The resulting red solution was stirred for 5 min at 0° C. and for 30 min at room temperature then treated at ambient temperature with a solution of the product of 5(f) (0.116 g, 0.325 mmol) in freshly distilled tetrahydrofuran (1.1 ml). Residual 52 was transferred to the reaction vessel with two 0.27 ml aliquots of freshly distilled tetrahydrofuran, and the reaction was stirred at reflux for 6 hours, cooled to 0° C., treated with diphenylphosphine (0.52 ml, 2.92 mmol) followed by n-butyllithium (1.8 ml, 2.85 mmol). The reaction was stirred for 5 min at 0° C., 20 min at ambient temperature and 18 hours at reflux, cooled to 0° C., acidified with cold, aqueous 1N HCl (12 ml) and diluted with ice-cold brine. The resulting suspension was extracted with ethyl acetate and the organics were washed with brine, dried over sodium sulfate, filtered and concentrated to a semi-solid.

The crude product was chromatographed on silica gel in 15% ethyl acetate in hexane to give 0.106 g (95%) of the title compound (g).

NMR (CDCl$_3$, TMS): δ 0.70–3.00 (m, 29, including doublet, 3 at 0.90, J=6 Hz), 3.23–3.57 (m, 1), 5.33–6.43 (m, 1), 6.63–6.90 (m, 2), 7.07 (d of d, 1).

Infrared (film): 3350, 2930, 2850, 1605, 1595, 1470, 1455, 1380, 1290, 1245, 1085, 1050, 1000, 895, 775, 740 cm$^{-1}$.

TLC (Silica Gel GF): Rf=0.31 in 25% ethyl acetate in hexane.

(h)

2-Cyano-15-cyclohexyl-2-decarboxy-9,11-dideoxy-13,14-dideoxy-2′,9α-methano-11-methyl-1,4,5,6,17,18,19,20-nonanor-3-oxa-3,7-(1′,3′-interphenylene)-PGF$_1$ and its 8,9,11,12-tetra-epi-isomer A degassed solution of the product of 5(g) (0.106 g, 0.309 mmol) in acetone (5 ml) was treated at ambient temperature under nitrogen with anhydrous potassium carbonate (0.915 g, 6.62 mmol), followed by chloroacetonitrile (0.71 ml, 11.25 mmol). The resulting suspension was stirred at reflux for 22 hours and was incomplete. Additional potassium carbonate (0.915 g, 6.62 mmol) and chloroacetonitrile (0.71 ml, 11.25 mmol) was added, and the reaction was stirred at reflux for 24 hours, cooled and diluted with 1:1 brine/water (75 ml). The suspension was extracted with ethyl acetate (3×75 ml), and the combined extracts were washed with brine (2×75 ml), dried over sodium sulfate, filtered and concentrated to a brown oil.

The crude product was chromatographed on silica gel acetone in methylene chloride to give 0.077 g (65%) of title compound (h).

NMR (CDCl$_3$, TMS): δ 0.70–3.03 (m, 29, including doublet, 3, J=6 Hz at 0.90), 3.20–3.53 (m, 1), 4.77 (s, 2), 6.73–7.03 (m, 2), 7.17 (d of d, $J_1=J_2=7.5$ Hz).

Infrared (film): 3400, 2930, 2850, 1605, 1590, 1480, 1475, 1375, 1260, 1235, 1100, 1045, 980, 895, 775, and 740 cm$^{-1}$.

TLC (Silica Gel GF): Rf=0.80 in 5% acetone in methylene chloride.

(i)

15-Cyclohexyl-9,11-dideoxy-13,14-dihydro-2′,9α-methano-11-methyl-4,5,6,16,17,18,19,20-octanor-3-oxa-3,7-(1′,3′-interphenylene)-PGF$_1$ A degassed solution of the nitrile compound 5(h) (0.077 g, 0.202 mmol) in anhydrous methanol (4.56 ml) was treated at ambient temperature under nitrogen with 25% aqueous potassium hydroxide (1.4 ml). The resulting solution was stirred at reflux for 5.5 hours, cooled to 0° C., acidified with aqueous 1N HCl (10 ml) and diluted with ice-cold brine (40 ml). The resulting suspension was extracted with ethyl acetate (3×50 ml), and the combined extracts were washed with brine (2×50 ml), dried over sodium sulfate, filtered and concentrated to an off-white solid which was recrystallized from ethyl acetate/hexane to give 0.056 g, (69%) of title compound (i), m.p. 123°–125° C.

NMR (CDCl$_3$, TMS): δ 0.70–3.10 (m, 28, including doublet, 3, J=6 Hz at 0.90), 3.20–3.53 (m, 1), 4.30 (bs, 2), 4.63 (s), 6.45–7.45 (m, 3).

Infrared (mull): 3430, 2970, 2860, 2720, 2580, 1740, SH(1705), 1605, 1590, 1465, 1425, 1380, 1260.

TLC (Silica Gel GF): Rf=0.32 in 1:1 A-IX-cyclohexane.

EXAMPLE 6

(a)

15-Cyclohexyl-9,11-dideoxy-13,14-dihydro-2′,9α-methano-11-methylene-1,4,5,6,16,17,18,19,20-nonanor-3-oxa-3,7-(1′,3′-interphenylene)-PGF$_1$ A solution of example 5(a) (0.195 g, 0.44 mmol) in acetic acid (6 ml) water (3 ml) and tetrahydrofuran (1.5 ml) was stirred for 3 hours at 45° C. under nitrogen, cooled, diluted with brine (75 ml) and extracted with ethyl acetate (3×75 ml). The organics were washed with brine (75 ml), aqueous saturated sodium bicarbonate (3×75 ml), and brine (2×75 ml), dried over sodium sulfate, filtered and the filtrate concentrated in vacuo to give a pale yellow oil.

The crude product was chromatographed in 10% ethyl acetate in hexane to afford 0.109 g (70%) of title compound (a).

NMR (CDCl$_3$, TMS): δ 0.73–3.10 (m, 24), 3.20–3.63 (m, 1 3.83 (s, 3), 4.77–5.07 (m, 2), 6.73–6.97 (m, 2), 7.13, (d of d, 1, J$_1$=J$_2$=7.5 Hz), 7.27–7.80 (m, 1).

Infrared (film): 3400, 3330, 2930, 2860, 1660, 1605, 1595, 1475, 1450, 1335, 1330, 1270, 1255, 1130, 1100, 1070, 1035, 965, 895, 875, 775, 754 cm$^{-1}$.

TLC (Silica Gel GF): Rf=0.47 in 20% ethyl acetate in hexane.

(b)

15-Cyclohexyl-1,2,4,5,6,16,17,18,19,20-decanor-9,11-dideoxy-13,14-dihydro-2',9α-methano-11-methylene-3-oxa-3,7-(1',3'-interphenylene)-PGF$_1$ A degassed solution of diphenylphosphine (0.16 ml, 0.90 mmol) in freshly distilled tetrahydrofuran (5 ml) was cooled to 0° C. under nitrogen and treated with 1.58M n-butyllithium in hexane (0.55 ml, 0.87 mmol). The resulting red solution was stirred at 0° C. for 5 minutes and at ambient temperature for 30 minutes then treated at room temperature with a solution of the methyl ester from 6(a) (0.106 g, 0.30 mml) in freshly distilled tetrahydrofuran (1 ml). The reaction was stirred at reflux for 6 hours, cooled to 0° C., treated with diphenylphosphine (0.32 ml, 1.80 mmol) followed by 1.58M n-butyllithium in hexane (1.10 ml, 1.74 mmol). The reaction was stirred at 0° C. for 5 minutes, at ambient temperature for 15 minutes and at reflux for 18 hours. The reaction was cooled to 0° C., diluted with brine (40 ml) containing 5 ml of 1N HCl, and extracted with ethyl acetate (3×35 ml). The organics were washed with brine (3×50 ml), dried over sodium sulfate, filtered and concentrated to a semi-solid.

The crude product was chromatographed on silica gel with 15% ethyl acetate in hexane to give 0.065 g (64%) of title product (b).

NMR (CDCl$_3$, TMS): δ 0.73–3.03 (m, 25), 3.27–3.6- (m, 1), 4.87 (d, 2, J=7 Hz), 5.10–5.97 (bs, 1), 6.70 (2d, 2, J1=J2=7.5 Hz).

Infrared (film): 3340, 2930, 2850, 1710 (weak), 1655, 1590, 1465, 1455, 1445, 1330, 1285, 1060, 1040, 880, 775, 735 cm$^{-1}$.

TLC (Silica Gel GF): Rf=0.29 in 25% in ethyl acetate in hexane.

(c)

2-Cyano-15-cyclohexyl-2-decarboxy-9,11-dideoxy-13,14-dihydro-2',9α-methano-11-methylene-1,4,5,6,16,17,18,19,20-nonanor-3-oxa-3,7-(1',3'-interphenylene)-PGF$_1$ A degassed solution of the phenol compound 6(b) (0.065 g, 0.19 mmol) in acetone (3 ml) was treated at ambient temperature under nitrogen with anhydrous potassium carbonate (0.566 g, 4.09 mmol) followed by chloroacetonitrile (0.44 ml, 6.97 mmol). The resulting suspension was stirred at reflux for 29.5 hours at reflux, cooled and diluted with 1:1 brine/water (50 ml). The suspension was extracted with ethyl acetate (3×50 ml), and the organics were washed with brine (2×50 ml), dried over sodium sulfate, filtered and concentrated to a brown oil.

The crude product was chromatographed on silica gel with ethyl acetate in hexane to give 0.067 g (93%) of title compound (c).

NMR (CDCl$_3$, TMS): δ 0.73–3.10 (m, 25), 3.23–3.63 (m, 1), 4.80 (s, 2), 4.87 (d, 2, J=7 HZ), 6.87 (2d, 2, J$_1$=J$_2$=7.5 Hz), 7.2 (d of d, 1, J$_1$=J$_2$=7.5 Hz).

Infrared (film): 3400, 3065, 2930, 2860, 1645, 1590, 1475, 1450, 1265, 1235, 1100, 885, 765 cm$^{-1}$.

TLC (Silica Gel GF): Rf=−0.54 in 5% acetone in methylene chloride.

(d)

15-Cyclohexyl-9,11-dideoxy-13,14-dihydro-2',9α-methano-11-methylene-4,5,6,16,17,18,19,20-octanor-3-oxa-3,7-(1',3'-interphenylene)-PGF$_1$ A degassed solution of the nitrile compound 6(c) (0.067 g, 0.177 mmol) in absolute methanol (4 ml) was treated at ambient temperature under nitrogen with 25% aqueous potassium hydroxide (1.4 ml). The resulting solution was stirred at reflux for 6 hours, cooled to 0° C., acidified to ∼pH 4 with 1N aqueous HCl (9.5 ml) and diluted with brine 35 (35 ml). The aqueous suspension was extracted with ethyl acetate (3×35 ml), and the combined organics were washed with brine (2×45 ml), dried over sodium sulfate, filtered and concentrated to a light yellow solid.

The crude product was recrystallized from ethyl acetate-hexane ∼1:10 to give a total of 60 mg (85%) of title compound (d).

NMR (CDCl$_3$, TMS): δ 0.73–3.10 (m, 24), 3.20–3.80 (m, 3), 4.63 (s, 2), 4.80 (d, 2, J=7 HZ), 6.58 (d, 1, J=7.5 Hz), 6.78 (d, 1, J=7.5 Hz), 7.05 (d of d, 1, J$_1$=J$_2$=7.5 Hz).

Infrared (nujol mull): 3350, 2930, 2860, 2550, 2430, 1715, 11605, 1590, 1470, 1440, 1375, 1335, 1255, 1235, 1115, 1040, 875 and 770 cm$^{-1}$.

TLC (Silica Gel GF): Rf=0.43 in 2 A-IX:1 cyclohexane, Rf=0.31 in 1:1-A-IX-cyclohexane.

FORMULA CHART

Formula I and Formula I(a)

Formula I(b)

Formula I(c)

Formula I(d)

FORMULA CHART

-continued

CHART A

-continued (a) $W_1$ = COOalkyl
(b) $W_1$ = CN
(c) $W_1$ = COOH

CHART B

| Formula | $W_2$ |
|---|---|
| XI | CHO |
| XII | trans-CH=CH-C(=O)-C(=L_2)(M_2)-R_7 |
| XII(a) | trans-CH=CH-C(=O)-C(=L_2)(M_2)-Rb |
| XIII | trans-CH=CH-C(=M_3)-C(=L_2)-R_7 |
| XIII(a) | trans-CH=CH-C(=M_3)-C(=L_2)-Rb |
| XIV | -CH_2CH_2-C(=M_3)-C(=L_2)-Ra |
| XIV(a) | -CH_2CH_2-C(=M_3)-C(=L_2)-Rb |
| XV | -CH_2CH_2-C(=M_3)-C(=L_2)-Rc |
| XVI | -C≡C-C(=M_3)-C(=L_2)-R_7 |
| XVI(a) | -C≡C-C(=M_3)-C(=L_2)-Rd |

CHART B-continued

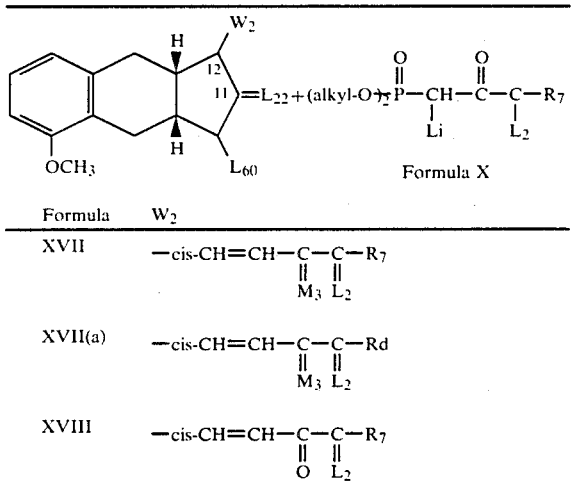

Formula X

| Formula | $W_2$ |
|---|---|
| XVII | $-\text{cis-CH}=\text{CH}-\underset{\underset{M_3}{\parallel}}{C}-\underset{\underset{L_2}{\parallel}}{C}-R_7$ |
| XVII(a) | $-\text{cis-CH}=\text{CH}-\underset{\underset{M_3}{\parallel}}{C}-\underset{\underset{L_2}{\parallel}}{C}-Rd$ |
| XVIII | $-\text{cis-CH}=\text{CH}-\underset{\underset{O}{\parallel}}{C}-\underset{\underset{L_2}{\parallel}}{C}-R_7$ |

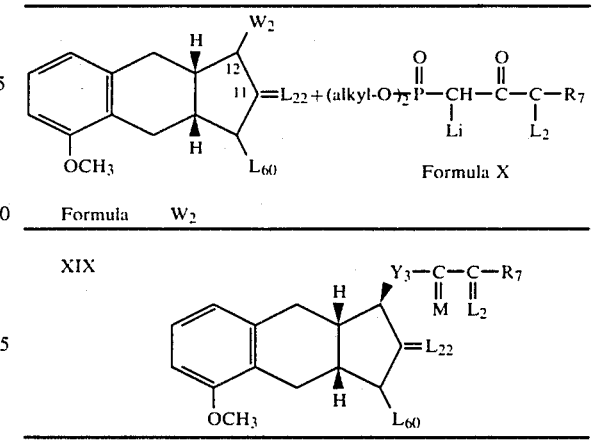

Formula X

| Formula | $W_2$ |
|---|---|
| XIX | |

CHART C

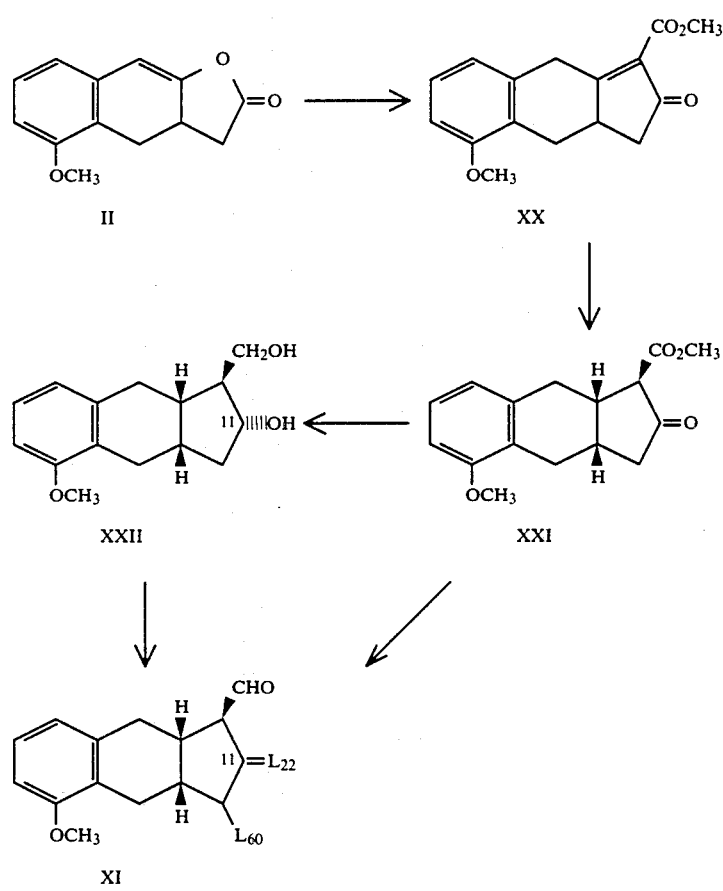

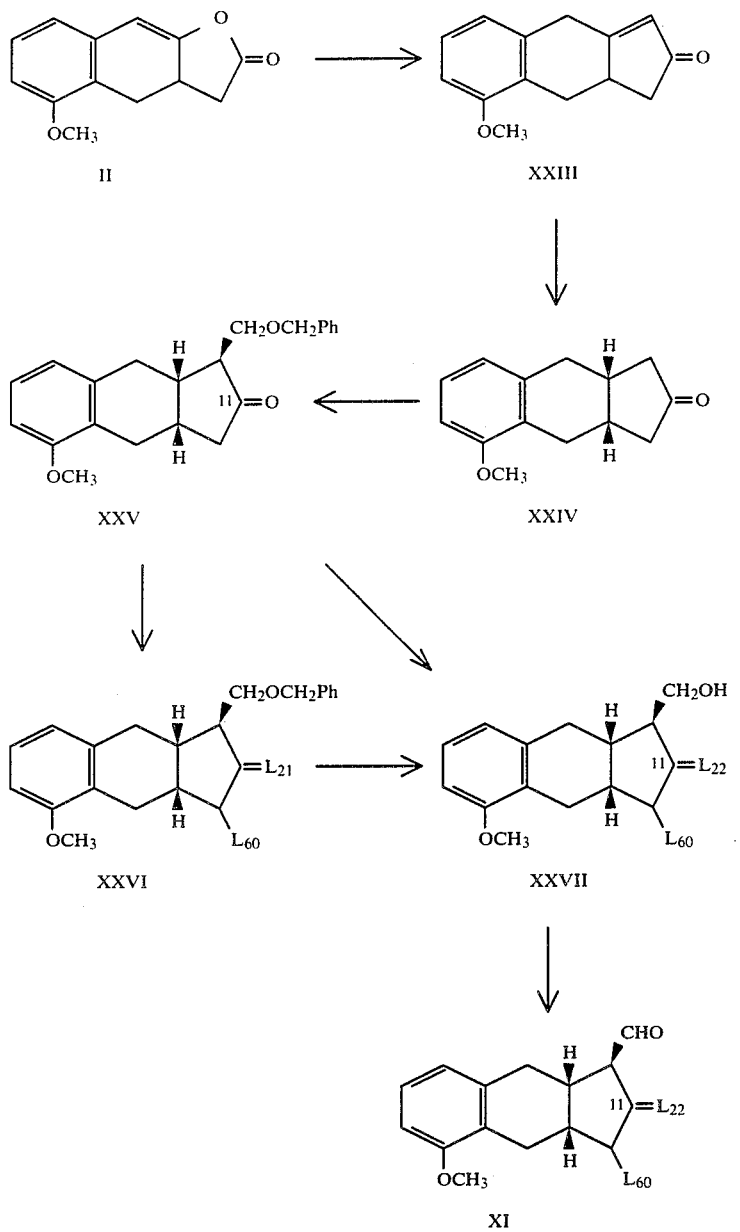
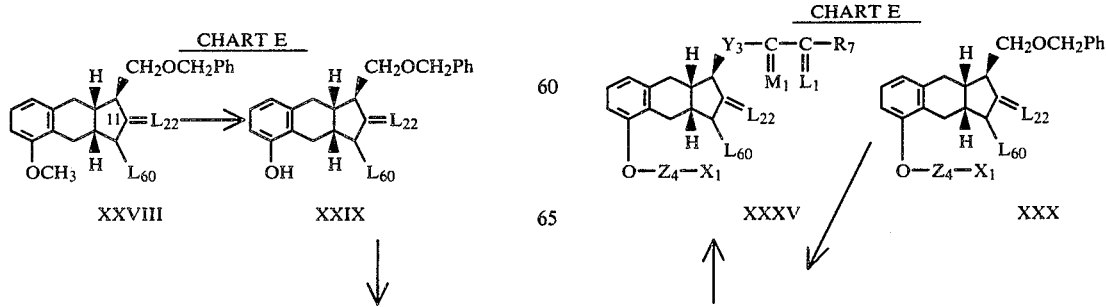

-continued CHART E
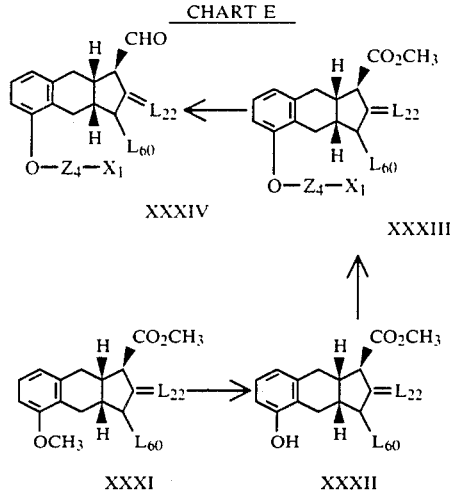
CHART G
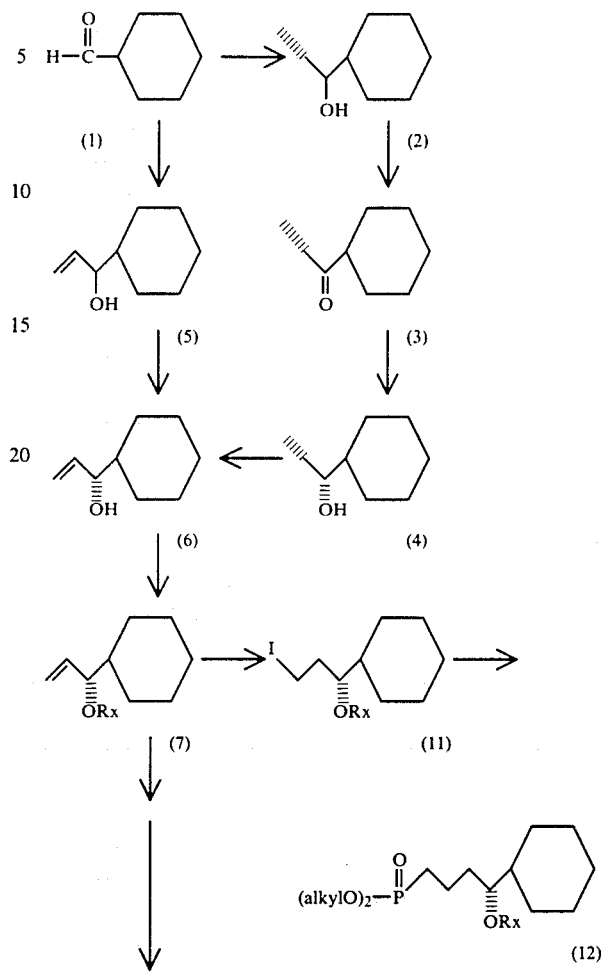
CHART F
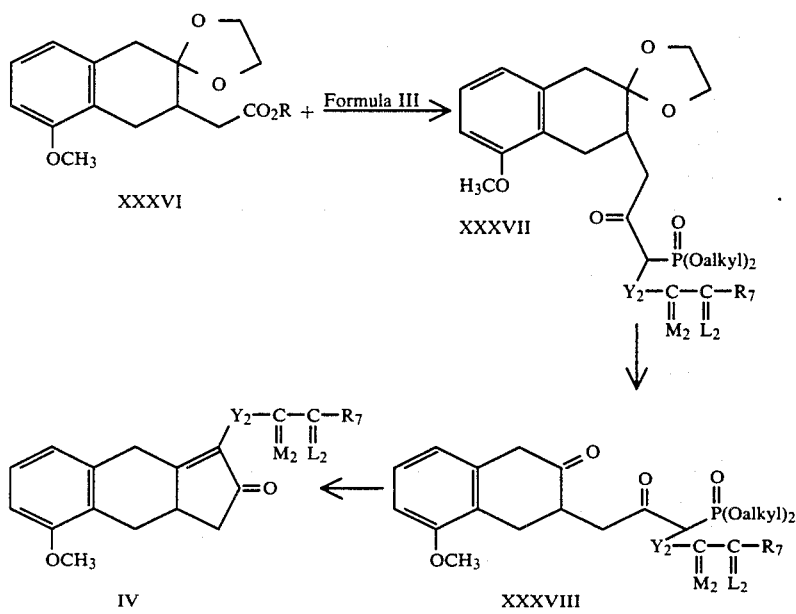

4,668,814
51
-continued
CHART G
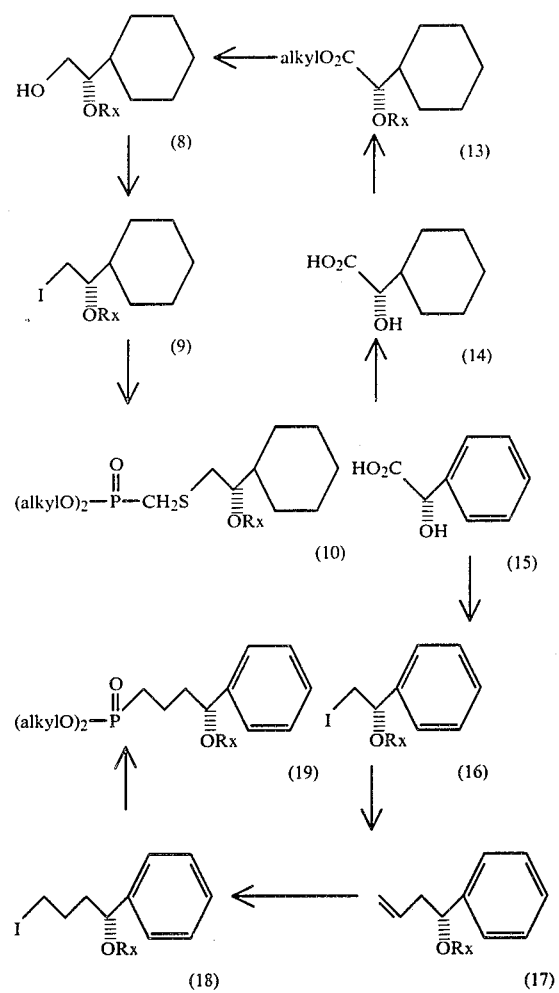
CHART H
HOCH₂C≡C—n-C₅H₁₁ ⟶ (20) (21)
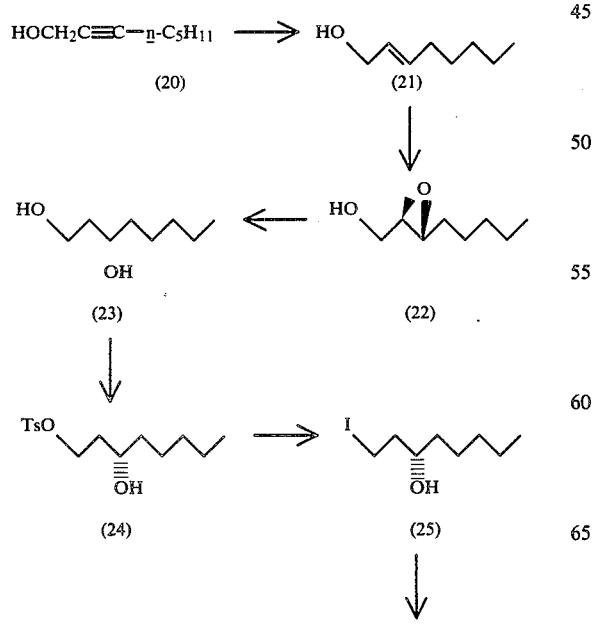
52
-continued
CHART H
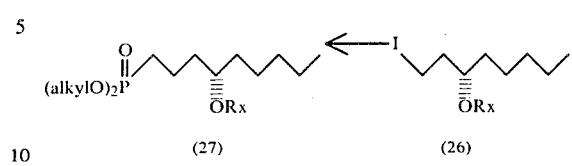
CHART J
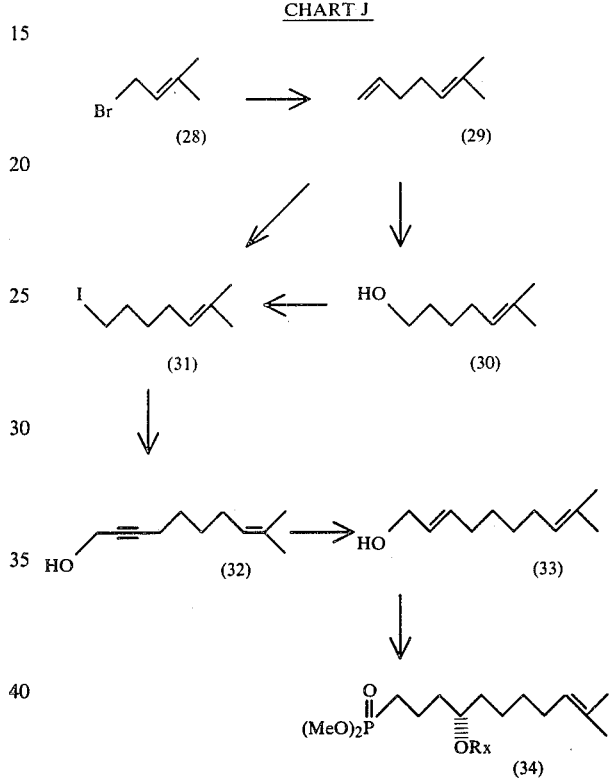
CHART K
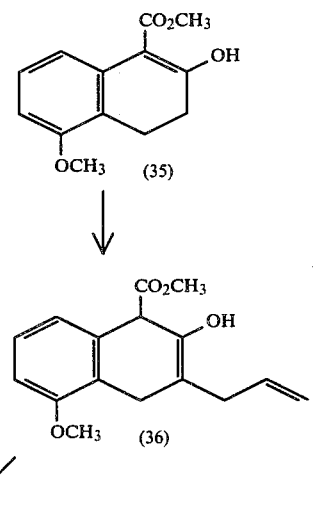

-continued
CHART K

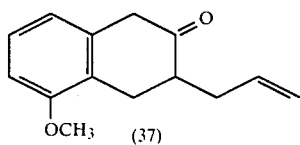
(37)

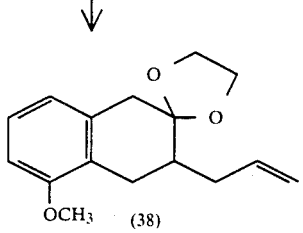
(38)

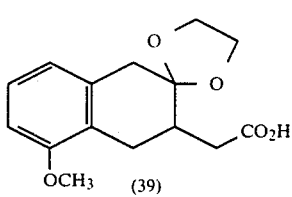
(39)

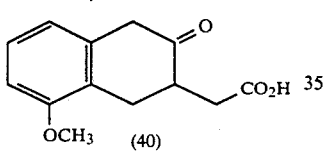
(40)

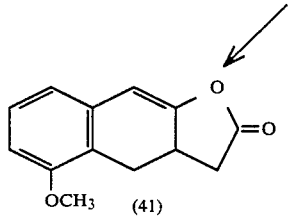
(41)

I claim:
1. A compound of the formula

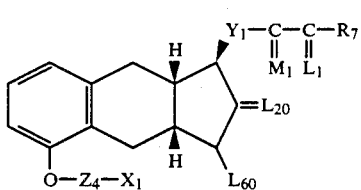

wherein $X_1$ is
(1) —$COOR_1$, wherein $R_1$ is
  (a) hydrogen;
  (b) ($C_1$-$C_{12}$) alkyl;
  (c) ($C_3$-$C_{10}$) cycloalkyl;
  (d) ($C_7$-$C_{12}$) aralkyl;
  (e) phenyl, optionally substituted with one, 2 or 3 chloro or ($C_1$-$C_3$) alkyl;
  (f) phenyl substituted in the para position by
    (i) —$NHCOR_{25}$,
    (ii) —$COR_{26}$,
    (iii)

$$-OCR_{54},$$
$$\parallel$$
$$O$$

or
    (iv) —CH=N—$NHCONH_2$ wherein $R_{25}$ is methyl, phenyl, acetamidophenyl, benzamidophenyl, or —$NH_2$; $R_{26}$ is methyl, phenyl, —$NH_2$, or methoxy; $R_{54}$ is phenyl or acetamidophenyl; inclusive; or
  (g) a pharmacologically acceptable cation;
(2) —$CH_2OH$;
(3) —$COL_4$, wherein $L_4$ is
  (a) amino of the formula —$NR_{51}R_{52}$ wherein $R_{51}$ and $R_{52}$ are
    (i) hydrogen,
    (ii) ($C_1$-$C_{12}$) alkyl,
    (iii) ($C_3$-$C_{10}$) cycloalkyl,
    (iv) ($C_7$-$C_{12}$) aralkyl,
    (v) phenyl, optionally substituted with one 2 or 3 chloro, ($C_1$-$C_3$) alkyl, hydroxy, carboxy, ($C_2$-$C_5$) alkoxycarbonyl, or nitro,
    (vi) ($C_2$-$C_5$) cyanoalkyl,
    (vii) ($C_2$-$C_5$) carboxyalkyl,
    (viii) ($C_2$-$C_5$) carbamoylalkyl,
    (ix) ($C_3$-$C_6$) acetylalkyl,
    (x) ($C_7$-$C_{11}$) benzoalkyl, optionally substituted by one, 2 or 3 chloro, ($C_1$-$C_3$) alkyl, hydroxy, ($C_1$-$C_3$) alkoxy, carboxy, ($C_2$-$C_5$) alkoxy carbonyl, or nitro,
    (xi) pyridyl, optionally substituted by one, 2 or 3 chloro, ($C_1$-$C_3$) alkyl, or ($C_1$-$C_3$) alkoxy,
    (xii) ($C_6$-$C_9$) pyridylalkyl optionally substituted by one, 2 or 3 chloro, ($C_1$-$C_3$) alkyl, hydroxy, or ($C_1$-$C_3$) alkoxy,
    (xiii) ($C_1$-$C_4$) hydroxyalkyl,
    (xiv) ($C_1$-$C_4$) dihydroxyalkyl,
    (xv) ($C_1$-$C_4$) trihydroxyalkyl, with the proviso that not more than one of $R_{51}$ or $R_{52}$ is other than hydrogen or alkyl;
  (b) cycloamino selected from the group consisting of pyrolidino, piperidino, morpholino, piperazino, hexamethylenimino, pyrrolino, or 3,4-didehydropiperidinyl optionally substituted by one or 2 ($C_1$-$C_{12}$) alkyl of one to 12 carbon atoms, inclusive;
  (c) carbonylamino of the formula —$NR_{53}COR_{51}$ wherein $R_{53}$ is hydrogen or ($C_1$-$C_4$) alkyl and $R_{51}$ is other than hydrogen, but otherwise defined as above;
  (d) sulfonylamino of the formula —$NR_{53}SO_2R_{51}$, wherein $R_{51}$ and $R_{53}$ are defined in (c);
(4) —$CH_2NL_2L_3$ wherein $L_2$ and $L_3$ are hydrogen or ($C_1$-$C_4$) alkyl, being the same or different, or the pharmacologically acceptable acid addition salts thereof when $X_1$ is —$CH_2NL_2L_3$;
(5) —CN;
wherein $Z_4$ is —$CH_2$—, —$CH_2CH_2$—, —$CF_2$—, or —$CH_2CF_2$;
wherein $L_{20}$ is α-OH,β-H; α-H,β-OH; H,H; α-$CH_3$,β-H; α-$CH_2OH$,β-H; =O; or =$CH_2$; wherein $L_{60}$ is hydrogen or $L_{20}$ and $L_{60}$ taken together form a double bond between positions 10 and 11;
wherein $Y_1$ is —$CH_2CH_2$—, —$SCH_2$—, —C≡C—, trans —CH=CH—, or cis —CH=CH—;

wherein

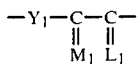

taken together is

wherein $M_1$ is $\alpha$-H:$\beta$-H; =O; $\alpha$-OH:$\beta$-$R_5$; or $\alpha$-$R_5$:$\beta$-OH; wherein $R_5$ is hydrogen or methyl;

wherein $L_1$ is
(1) $\alpha$-$R_3$:$\beta$-$R_4$, $\alpha$-$R_4$:$\beta$-$R_3$, or mixtures thereof wherein $R_3$ and $R_4$ are hydrogen, methyl, or fluoro, being the same or different, with the proviso that one of $R_3$ and $R_4$ is fluoro only when the other is hydrogen or fluoro;
(2) or when $M_1$ is $\alpha$-H:$\beta$-H $L_1$ is $\alpha$-OH:$\beta$-$R_3$, $\alpha$-$R_3$:$\beta$-OH; or a mixture of $\alpha$-OH:$\beta$-$R_3$ and $\alpha$-$R_3$:$\beta$-OH wherein $R_3$ is hydrogen, methyl, vinyl, or ethynyl;

wherein $R_7$ is
(1) —$C_mH_{2m}CH_3$, wherein m is an integer from one to 8, inclusive;
(2) phenoxy optionally substituted by one, 2 or 3 chloro, fluoro, trifluoromethyl, ($C_1$-$C_3$) alkyl, or ($C_1$-$C_3$) alkoxy, with the proviso that not more than two substituents are other than alkyl with the proviso that $R_7$ is phenoxy or substituted phenoxy, only when $R_3$ and $R_4$ are hydrogen or methyl, being the same or different;
(3) phenyl, benzyl, phenylethyl, or phenylpropyl optionally substituted on the aromatic ring by one, 2 or 3 chloro, fluoro, trifluoromethyl, ($C_1$-$C_3$) alkyl, or ($C_1$-$C_3$) alkoxy, with the proviso, that not more than two substituents are other than alkyl;
(4) cis —CH=CH—$CH_2CH_3$;
(5) —$(CH_2)_2$—CH(OH)—$CH_3$;
(6) —$(CH_2)_3$—CH=C$(CH_3)_2$;
(7) —$(CH_2)_2$—CH=$CH_2$;
wherein

taken together is
(1) ($C_4$-$C_7$) cycloalkyl optionally substituted by one to 3 ($C_1$-$C_5$) alkyl or ($C_1$-$C_5$) alkenyl;
(2) 2-(2-furyl)ethyl;
(3) 2-(3-thienyl)ethoxy;
(4) 3-thienyloxymethyl;
(5)

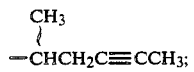

and the individual optical enantiomers thereof with the proviso that each compound is other than one formed when the substituents $X_1$, $Z_4$, $L_{20}$, $Y_1$, $L_1$, and $R_7$ have the following meanings:
wherein $X_1$ is as defined above;
wherein $Z_4$ is —$CH_2$—, —$CF_2$, or —$CH_2CF_2$—;
wherein $L_{20}$ is $\alpha$-OH,$\beta$-H; $\alpha$-H,$\beta$-OH; H,H; $\alpha$-$CH_2OH$,$\beta$-H;

wherein $Y_1$ is —$CH_2CH_2$—, —C≡C—, trans —CH=CH—, or cis —CH=CH—;
wherein $M_1$ is $\alpha$-OH:$\beta$-$R_5$, or $\alpha$-$R_5$:$\beta$-OH wherein $R_5$ is hydrogen or methyl;
wherein $L_1$ is
(1) $\alpha$-$R_3$:$\beta$-$R_4$, $\alpha$-$R_4$:$\beta$-$R_3$, or a mixture of $\alpha$-$R_3$:$\beta$-$R_4$, wherein $R_3$ and $R_4$ are hydrogen, methyl, or fluoro, being the same or different, with the proviso that one of $R_3$ and $R_4$ is fluoro only when the other is hydrogen or fluoro; and
wherein $R_7$ is as defined above except $R_7$ is other than —$(CH_2)_2$—CH=$CH_2$ and $C(L_1)R_7$ taken together is as defined above except $C(L_1)R_7$ is other than ($C_4$-$C_7$) cycloalkyl optionally substituted with ($C_1$-$C_5$) alkenyl.

2. A compound of claim 1 wherein $M_1$ is $\alpha$-H,$\beta$-OH; $\alpha$-OH,$\beta$-H, or H,H.

3. A compound of claim 2 wherein $L_{20}$ is $\alpha$-$CH_3$,$\beta$-H or $\alpha$-OH,$\beta$-H.

4. A compound of claim 3 wherein $Z_4$ is —$CH_2$—.

5. A compound of claim 3 wherein $X_1$ is $COOR_1$.

6. A compound of claim 5 wherein $R_1$ is hydrogen, or ($C_1$-$C_{12}$) alkyl or a pharmaceutically acceptable cation.

7. A compound of claim 3 wherein $R_7$ is —$C_mH_{2m}CH_3$ wherein m is an integer from one to 8 inclusive, —$(CH_2)_2$—CH=$CH_2$, or —$(CH_2)_3$—CH=CH($CH_3)_2$.

8. A compound of claim 3 wherein —C($L_1$)$R_7$ taken together is ($C_4$-$C_7$) cycloalkyl.

9. A compound of claim 1 which is (11RS,15R)-15-cyclohexyl-9,11-dideoxy-13,14-dihydro-2',9$\alpha$-methano-11-methyl-4,5,6,16,17,18,18,20-octanor-3-oxa-3,7-(1',3'-interphenylene)$PGF_1$ and salts and isomers thereof.

10. A compound of claim 1 which is (15R)-15-cyclohexyl-9,11-dideoxy-13,14-dihydro-2',9$\alpha$-methano-11-methylene-4,5,6,16,17,18,19,20-octanor-3-oxa-3,7-(1',3'-interphenylene)$PGF_1$ and salts and isomers thereof.

11. A compound of formula

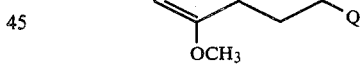

Formula I(b)

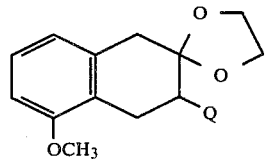

Formula I(c)

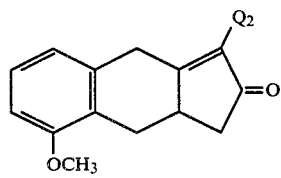

Formula I(d)

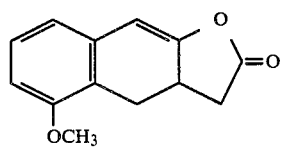

Formula II wherein Q is cis-$CH_2CH=CH_2$, $-CH_2COOH$, or

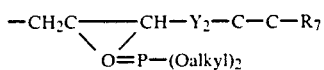

wherein alkyl has from 1 to 4 carbon atoms, $Y_2$ is $-SCH_2-$ or $CH_2CH_2-$, $M_2$ is $\alpha$-H:$\beta$-$OR_x$, $\alpha$-$OR_x$:$\beta$-H or H,H wherein $R_x$ is a protecting group; $L_2$ is $\alpha$-$R_3$:$\beta$-$R_4$, $\alpha$-$R_4$:$\beta$-$R_3$ or mixture thereof wherein $R_3$ and $R_4$ are hydrogen, methyl or fluoro, being the same or different with the proviso that one of $R_3$ and $R_4$ is fluoro only when the other is hydrogen or fluoro, or when $M_2$ is H,H, $L_2$ is $\alpha$-$OR_x$:$\beta$-$R_3$, $\alpha$-$R_3$:$\beta$-$OR_x$, or a mixture thereof wherien $R_3$ is hydrogen, methyl, vinyl or ethynyl and $R_x$ is a protecting group; and $R_7$ (1) $-C_mH_{2m}CH_3$, wherein m is an integer from one to 8, inclusive;
(2) phenoxy optionally substituted by one, 2 or 3 chloro, fluoro, trifluoromethyl, ($C_1$-$C_3$) alkyl, or ($C_1$-$C_3$) alkoxy, with the proviso that not more than two substituents are other than alkyl with the proviso that $R_7$ is phenoxy or substituted phenoxy, only when $R_3$ and $R_4$ are hydrogen or methyl, being the same or different;
(3) phenyl, benzyl, phenylethyl, or phenylpropyl optionally substituted on the aromatic ring by one, 2 or 3 chloro, fluoro, trifluoromethyl, ($C_1$-$C_3$) alkyl, or ($C_1$-$C_3$) alkoxy, with the proviso that not more than two substituents are other than alkyl;
(4) cis-$CH=CH-CH_2CH_3$;
(5) $-(CH_2)_2-CH(OH)-CH_3$;
(6) $-(CH_2)_3-CH=C(CH_3)_2$;
(7) $-C_pH_{2p}CH=CH_2$ wherein p is an integer from 2 to 6, inclusive;

or C—$R_7$ taken together is (1) ($C_4$-$C_7$) cycloalkyl optionally substituted by one to 3 ($C_1$-$C_5$) alkyl, or ($C_1$-$C_5$)alkenyl;
(2) 2-(2-furyl)ethyl;
(3) 2-(3-thienyl)ethoxy;
(4) 3-thienyloxymethyl; or
(5)

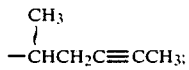

and
$Q_2$ is

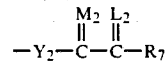

wherein $Y_2$, $M_2$, $L_2$ and $R_7$ are as defined above or $Q_2$ is $-CO_2$ alkyl wherein alkyl has from 1 to 4 carbon atoms.

* * * * *

UNITED STATES PATENT OFFICE
CERTIFICATE OF CORRECTION

Patent No. 4,668,814　　　　　　　　Dated　26 May 1987

Inventor(s)　Paul A. Aristoff

It is certified that error appears in the above-identified patent and that said Letters Patent are hereby corrected as shown below:

Column 1, line 9, should read:

CROSS REFERENCE TO RELATED APPLICATIONS: This application is a C-I-P of U.S. application Serial No. 587,337, filed March 8, 1984, now abandoned.

Signed and Sealed this

Ninth Day of August, 1988

Attest:

DONALD J. QUIGG

Attesting Officer　　　Commissioner of Patents and Trademarks